US011071565B2

(12) United States Patent
Weng et al.

(10) Patent No.: US 11,071,565 B2
(45) Date of Patent: Jul. 27, 2021

(54) METHOD AND DEVICE OF MALE CIRCUMCISION AND SUTURE

(71) Applicants: Xiaofeng Weng, Changshu (CN); Zhijiang Weng, Changshu (CN); Yuguo Zhu, Temple City, CA (US)

(72) Inventors: Xiaofeng Weng, Changshu (CN); Zhijiang Weng, Changshu (CN); Yuguo Zhu, Temple City, CA (US)

( * ) Notice: Subject to any disclaimer, the term of this patent is extended or adjusted under 35 U.S.C. 154(b) by 166 days.

(21) Appl. No.: 15/681,416

(22) Filed: Aug. 20, 2017

(65) Prior Publication Data
US 2018/0055528 A1 Mar. 1, 2018

Related U.S. Application Data

(60) Provisional application No. 62/538,783, filed on Jul. 30, 2017.

(30) Foreign Application Priority Data

Aug. 24, 2016 (CN) .......................... 201620926070.4
Aug. 24, 2016 (CN) .......................... 201620926090.1
(Continued)

(51) Int. Cl.
A61B 17/326 (2006.01)
A61B 17/068 (2006.01)
(Continued)

(52) U.S. Cl.
CPC ........ A61B 17/326 (2013.01); A61B 17/0469 (2013.01); A61B 17/068 (2013.01); A61B 17/1155 (2013.01)

(58) Field of Classification Search
CPC . A61B 17/326; A61B 17/1155; A61B 17/068; A61B 17/0469
See application file for complete search history.

(56) References Cited

U.S. PATENT DOCUMENTS

2003/0183671 A1* 10/2003 Mooradian .......... A61B 17/115
227/175.1
2008/0004654 A1* 1/2008 Tomlinson ........... A61B 17/326
606/201
2010/0168757 A1* 7/2010 Tomlinson ........... A61B 17/326
606/118

FOREIGN PATENT DOCUMENTS

CN 103750886 * 4/2014 .......... A61B 17/326
WO WO-2015010477 A1 * 1/2015 .......... A61B 17/326

* cited by examiner

Primary Examiner — Shaun L David
Assistant Examiner — Christina C Lauer
(74) Attorney, Agent, or Firm — Raymond Y. Chan; David and Raymond Patent Firm

(57) ABSTRACT

A male circumcision and suture device includes a glans receiver socket including a glans socket for inserting into an excess foreskin of a patient and a socket shaft extended from the glans socket, an operation housing having a shaft channel extended from a front edge, an annular cutter coaxially coupled at the front edge of the operation housing, a plurality of staples spacedly disposed at the front edge of the operation housing, and two operation handles pivotally coupled at the operation housing to actuate the annular cutter and the staples at the same time. When the operation handles to are concurrently and pivotally actuated, the annular cutter is pushed out of the front edge of the operation housing for removing the excess foreskin of the patient and at the same time, the staples are pushed for applying stitches at a cut area of the excess foreskin of the patient.

16 Claims, 17 Drawing Sheets

(30) Foreign Application Priority Data

Aug. 24, 2016 (CN) .......................... 201620926094.X
Aug. 24, 2016 (CN) .......................... 201620926121.3

(51) Int. Cl.
*A61B 17/04* (2006.01)
*A61B 17/115* (2006.01)

METHOD AND DEVICE OF MALE CIRCUMCISION AND SUTURE

CROSS REFERENCE OF RELATED APPLICATION

This is a non-provisional application that claims the benefit of priority under 35 U.S.C.§ 120 to a provisional application, application No. 62/538,783, filed Jul. 30, 2017, and claims priority under 35 U.S.C. 119(a-d) to Chinese application number 201620926090.1, filed Aug. 24, 2016, Chinese application number 201620926121.3, filed Aug. 24, 2016, Chinese application number 201620926070.4, filed Aug. 24, 2016, and Chinese application number 201620926094.X, filed Aug. 24, 2016. The afore-mentioned patent applications are hereby incorporated by reference in their entireties.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to the field of circumcision, and more particularly to a method and device for male circumcision and suture, which can precisely remove excess foreskin from the penis during circumcision and, at the same time, can rapidly apply stitches to the cut area of the skin in one single operative motion.

Description of Related Arts

Circumcision is the most common surgical procedure for removing excess foreskin from the penis of the patient, especially for the newborn boy, in the United States. For some families, circumcision is a religious ritual and can be personal hygiene.

There are two major concerns during the circumcision procedure are uneven incision and bleeding. Generally speaking, a glans ring is inserted into and placed underneath foreskin, wherein a circumferential edge of the glans ring serves as a cutting guidance. Then, the surgeon can perform incision for cutting the excess foreskin along the circumferential edge of the glans ring and apply stitches to the cut area. The major drawback of the glans ring is the corrected placement of the glans ring that the amount of foreskin to be excised. If the glans ring is eccentrically placed over the glans underneath the foreskin, the excess foreskin cannot be precisely removed when the surgeon performs incision. Also, it is hard for the surgeon to apply stitches with the uneven incision in order to stop the bleeding.

SUMMARY OF THE PRESENT INVENTION

The invention is advantageous in that it provides a method and device for male circumcision and suture, which can precisely remove excess foreskin from the penis during circumcision and, at the same time, can rapidly apply stitches to the cut area of the skin in one single operative motion.

Another advantage of the invention is to a method and device for male circumcision and suture, wherein the excess foreskin of the patient is securely retained between the front edge of the operation housing and the guiding seat of the glans socket, such that the actuation of the annular cutter will ensure an even incision of the excess foreskin.

Another advantage of the invention is to a method and device for male circumcision and suture, wherein the cutter is actuated by the concurrent pressing forces at the operation handles toward the operation housing. In other words, the pressing forces must be evenly applied toward the operation housing to ensure the alignment of the annular cutter with the glans socket.

Another advantage of the invention is to a method and device for male circumcision and suture, wherein the cutter and the staple pusher arms are actuated by a single driving shaft to ensure the cutting operation by the annular cutter and the stitching operation by the staples to be performed at the same time.

Another advantage of the invention is to a method and device for male circumcision and suture, wherein the socket shaft of the glans socket has a predetermined length corresponding to the shaft channel of the operation housing to ensure the placement of the glans receiver socket.

Another advantage of the invention is to a method and device for male circumcision and suture, wherein the staples are held by an annular holding band to ensure the corrected alignment of the staples to be evenly spaced apart with each other and to provide a buffering clearance between the staples and the cut area of the patient so as to prevent the direct stapling contact of the staples to the cut area of the patient.

Another advantage of the invention is to a method and device for male circumcision and suture, wherein each of the operation handles is made of breakable material having a safety factor to prevent the over pressing force applied on the operation handles. For example, the operation handle will be broken if the pressing force is larger than 45 kg.

Another advantage of the invention is to a method and device for male circumcision and suture, wherein the male circumcision and suture operation is simple, rapid, and easy by a single action of the operation handle, so as to substantially reduce the significant amount of the pain and trauma associated with the circumcision.

Additional advantages and features of the invention will become apparent from the description which follows, and may be realized by means of the instrumentalities and combinations particular point out in the appended claims.

According to the present invention, the foregoing and other objects and advantages are attained by a device for male circumcision and suture, comprising:

a glans receiver socket which comprises a glans socket for inserting into and placed underneath an excess foreskin of a patient to cover a glans thereof, and a socket shaft extended from the glans socket, wherein the glans socket has a guiding seat coaxially aligned with the socket shaft;

a hollow operation housing having a circular front edge, a rear edge, and a shaft channel extended from the front edge to the rear edge, wherein the socket shaft slidably passes through the shaft channel until the front edge of the operation housing is biased against the guiding seat of the glans socket for retaining the excess foreskin of the patient between the front edge of the operation housing and the guiding seat of the glans socket;

an annular cutter retractably and coaxially coupled at the front edge of the operation housing;

a suture cartridge which comprises a plurality of staples spacedly disposed at the front edge of the operation housing; and two operation handles pivotally coupled at the operation housing to actuate the annular cutter and the suture cartridge at the same time, wherein when the operation handles are concurrently and pivotally moved toward the operation housing, the annular cutter is pushed out of the front edge of the operation housing to contact with the guiding seat of the glans socket for removing the excess foreskin of the patient and at the same time, the staples are pushed to contact with the guiding seat of the glans socket for applying stitches at a cut area of the excess foreskin of the patient.

In accordance with another aspect of the invention, the present invention comprises an operating method for male circumcision and suture, comprising the following steps.

(A) Provide a glans receiver socket which comprises a glans socket having a guiding seat, and a socket shaft extended from the glans socket.

(B) Insert the glans socket of the glans receiver socket into an excess foreskin of a patient to cover a glans thereof.

(C) Slide the socket shaft into a shaft channel of an operation housing until a front edge of the operation housing biased against the guiding seat of the glans socket for retaining the excess foreskin of the patient between the front edge of the operation housing and the guiding seat of the glans socket.

(D) Secure the socket shaft at the shaft channel to lock up the glans socket at the front edge of the operation housing.

(E) Pivotally actuate two operation handles at the operation housing to actuate an annular cutter and a suture cartridge at the same time.

In accordance with another aspect of the invention, the present invention comprises a method of assembling a device for male circumcision and suture, comprising the following steps.

(1) Dispose a suture cartridge at a front edge of an operation housing;

(2) Cover a safety cap at the front edge of the operation housing to enclose the suture cartridge and an annular cutter which is provided at the front edge of the operation housing.

(3) Slidably insert a socket shaft of a glans receiver socket into a shaft channel of the operation housing until a glans socket of the glans receiver socket is biased against the front edge of the operation housing to retain the safety cap between the glans socket and the front edge of the operation housing.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Referring to FIGS. 1 to 5 of the drawings, a device for male circumcision and suture according to a preferred embodiment of the present invention is illustrated, wherein the device of the present invention can precisely remove excess foreskin from the penis of the patient during circumcision and, at the same time, can rapidly apply stitches to the cut area of the skin. The device comprises a glans receiver socket 10, a hollow operation housing 20, an annular cutter 30, and a suture cartridge 40.

Figure 6:
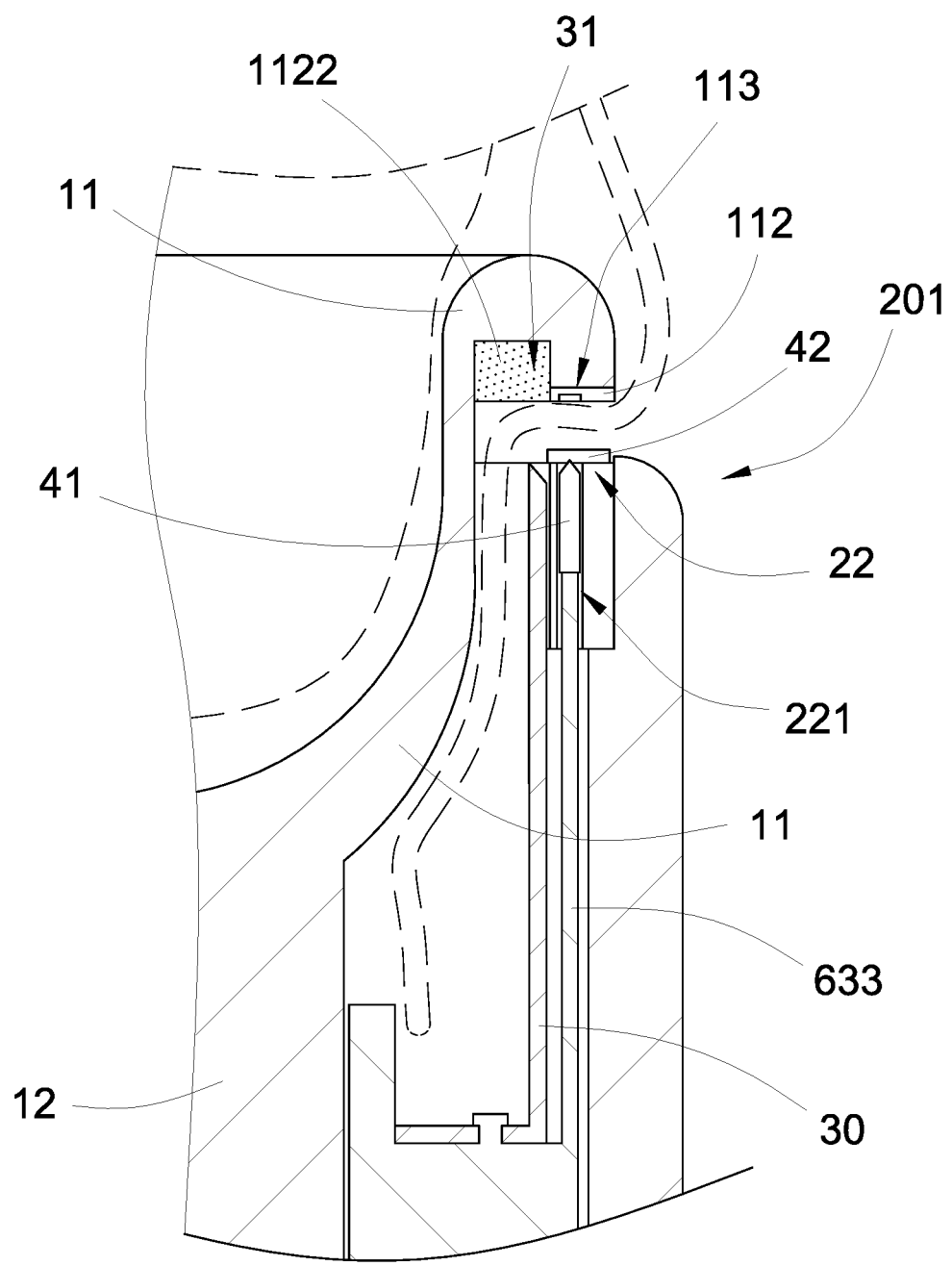
FIG. 6 illustrates the excess foreskin of the patient to be secured between the front edge of the operation housing and the guiding seat of the glans socket of the device for male circumcision and suture according to the above preferred embodiment of the present invention.
Figure 7:
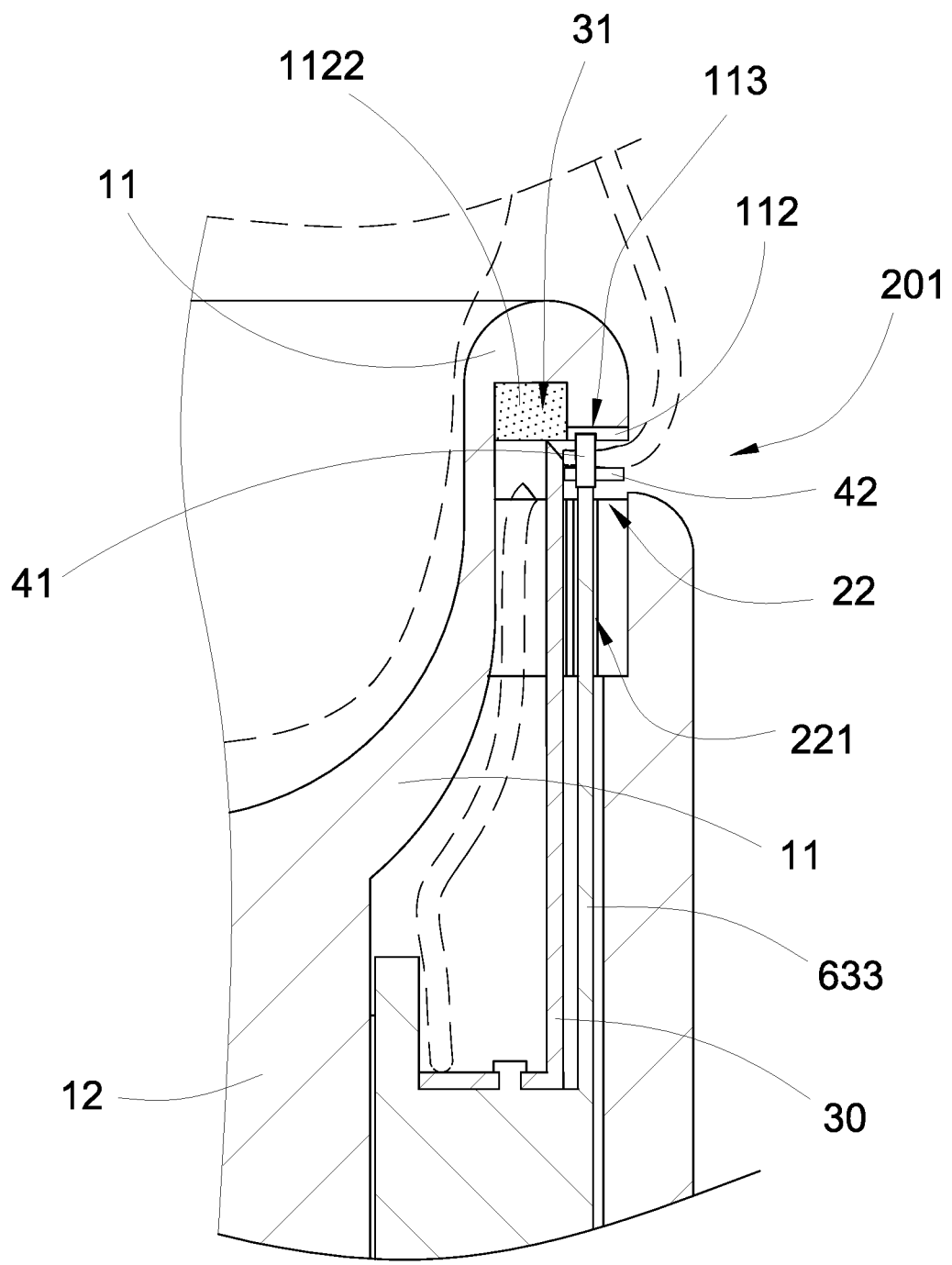
FIG. 7 illustrates the annular cutter and the suture cartridge being actuated at the same time for removing the excess foreskin of the patient and at the same time for applying stitches at a cut area of the excess foreskin of the patient according to the above preferred embodiment of the present invention.

According to the preferred embodiment, the glans receiver socket 10 comprises a glans socket 11 and a socket shaft 12 extended from the glans socket 11. The glans socket 11 is arranged for inserting into and placed underneath the excess foreskin of the patient to cover the glans thereof, so as to protect the glans during operation, as shown in FIGS. 6 and 7. When the glans socket 11 is placed underneath the excess foreskin, the socket shaft 12 is extended out of the excess foreskin of the patient. Preferably, the glans socket 11 has a conical shape defining a glans chamber 110 for covering and protecting the glans of the patient, wherein the socket shaft 12 is extended from an apex of the glans socket 11. The glans socket 11 further comprises a front rim 111 having an annular shape and a guiding seat 112 provided at a rear side of the front rim 111 and coaxially aligned with the socket shaft 12. The guiding seat 112 comprises an outer seat portion 1121 and an inner seat portion 1122. The outer seat portion 1121 of the guiding seat 112 is preferably made of metal and is configured to have an annular shape, has a plurality of staple guiding indentions 113 spacedly formed at the outer seat portion of the guiding seat 112. The inner seat portion 1122 of the guiding seat 112 is preferably made of cushioning material, such as rubber or soft plastic.

The operation housing 20, which is configured to have a hollow structure, has a circular front edge 201, a rear edge 202, and a shaft channel 203 extended from the front edge 201 to the rear edge 202 to define a front opening at the front edge 201 and a rear opening at the rear edge 202, wherein the socket shaft 112 slidably passes through the shaft channel 203 from the front edge 201 toward the rear edge 202. Accordingly, a diameter size of the front edge 201 of the operation housing 20 matches with a diameter size of the glans socket 11. In particular, the diameter size of the front edge 201 of the operation housing 20 matches with a diameter size of the front rim 111 of the glans socket 11. The socket shaft 112 is slid through the shaft channel 203 until the front edge 201 of the operation housing 20 is biased against the guiding seat 112 of the glans socket 11 for retaining the excess foreskin of the patient between the front edge 201 of the operation housing 20 and the guiding seat 112 of the glans socket 11. It is worth mentioning that when the socket shaft 112 is slid into the shaft channel 203, the glans receiver socket 10 should not be pulled from the glans of the patient to avoid incorrect cutting after the foreskin slides down.

In particular, when the socket shaft 112 is slid through the shaft channel 203, the excess foreskin of the patient will also receive in the shaft channel 203, such that the excess foreskin of the patient will be clamped and sandwiched between the front edge 201 of the operation housing 20 and the guiding seat 112 of the glans socket 11. It is worth mentioning that the conical shaped glans socket 11 will guide the excess foreskin of the patient to overlap on the conical surface for guiding the excess foreskin of the patient to insert into the shaft channel 203 through the front edge 201 of the operation housing 20.

Figure 1:
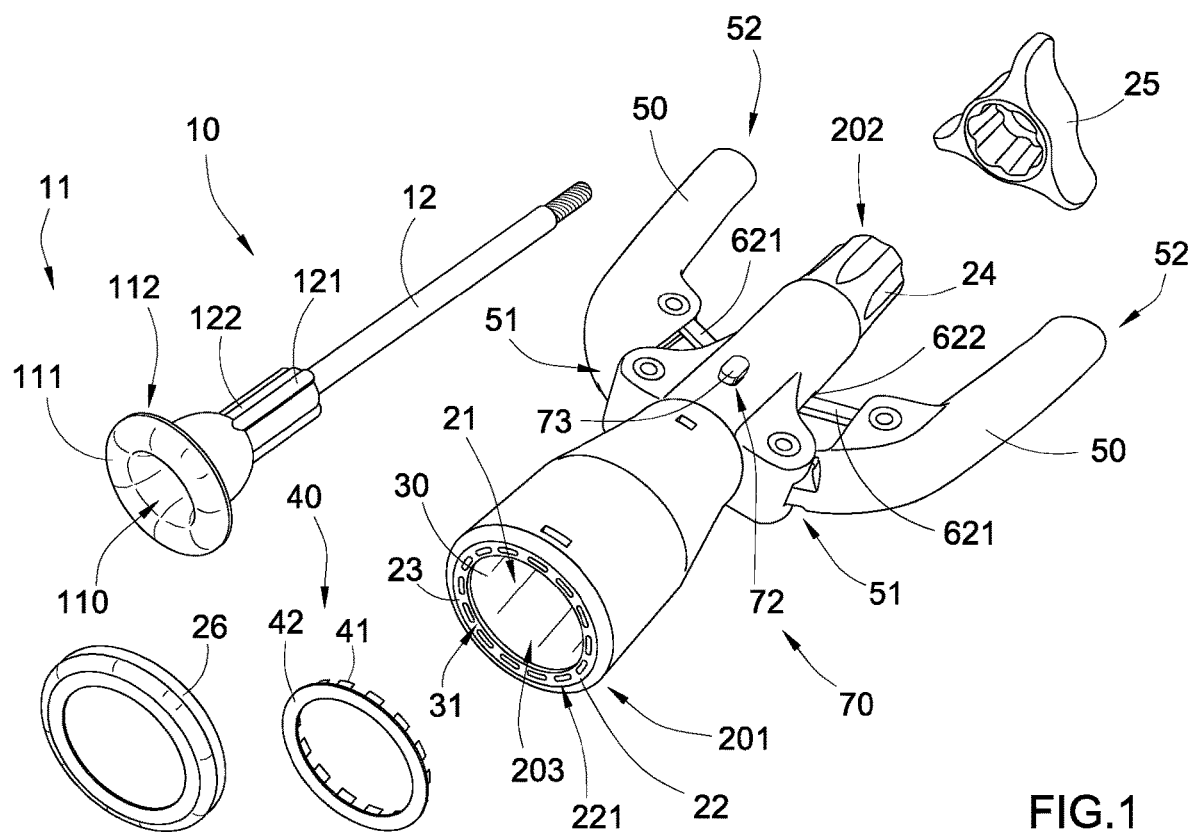
FIG. 1 is an exploded perspective view of a device for male circumcision and suture according to a preferred embodiment of the present invention.
Figure 2:
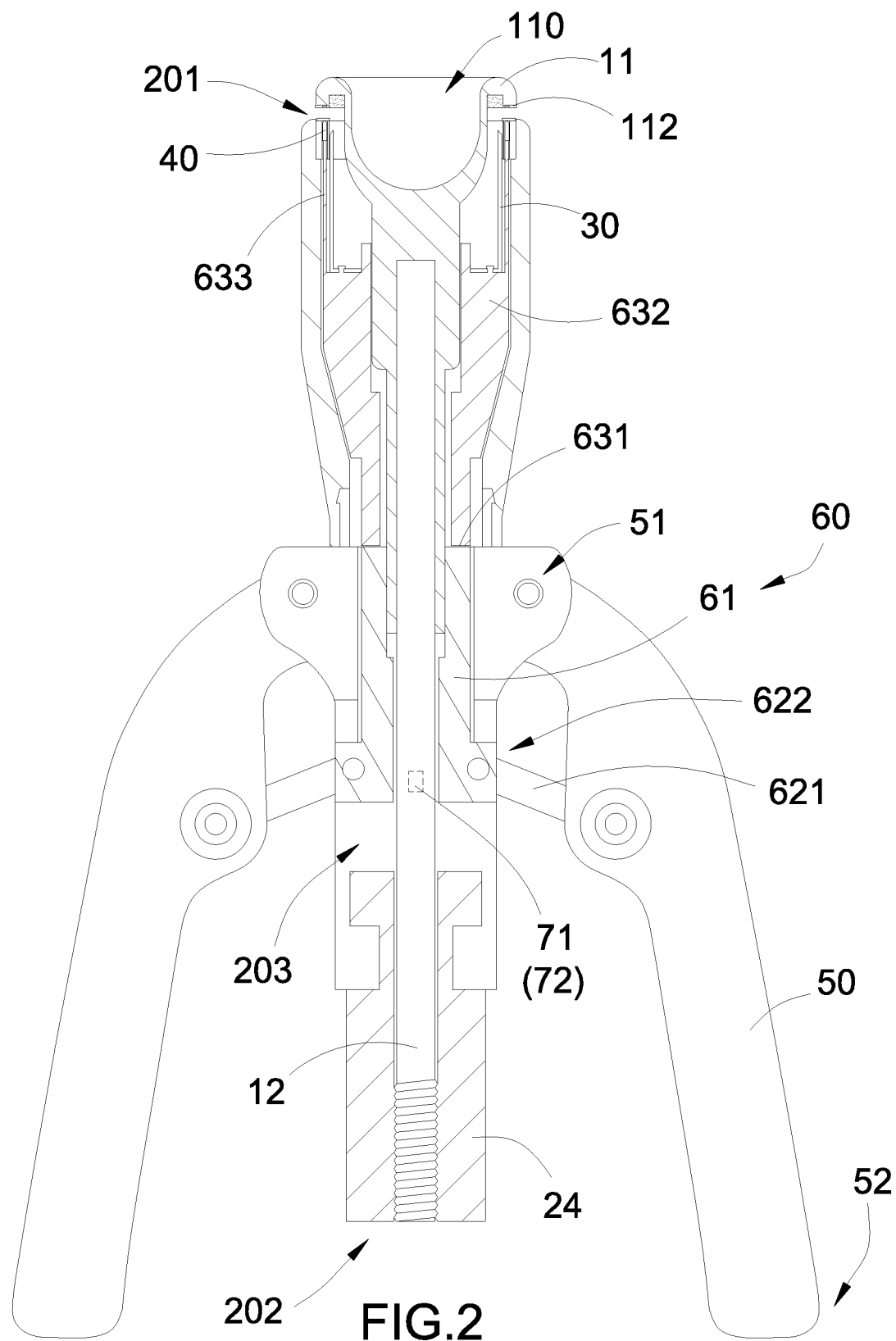
FIG. 2 is a sectional view of the device for male circumcision and suture according to the above preferred embodiment of the present invention.
Figure 3:
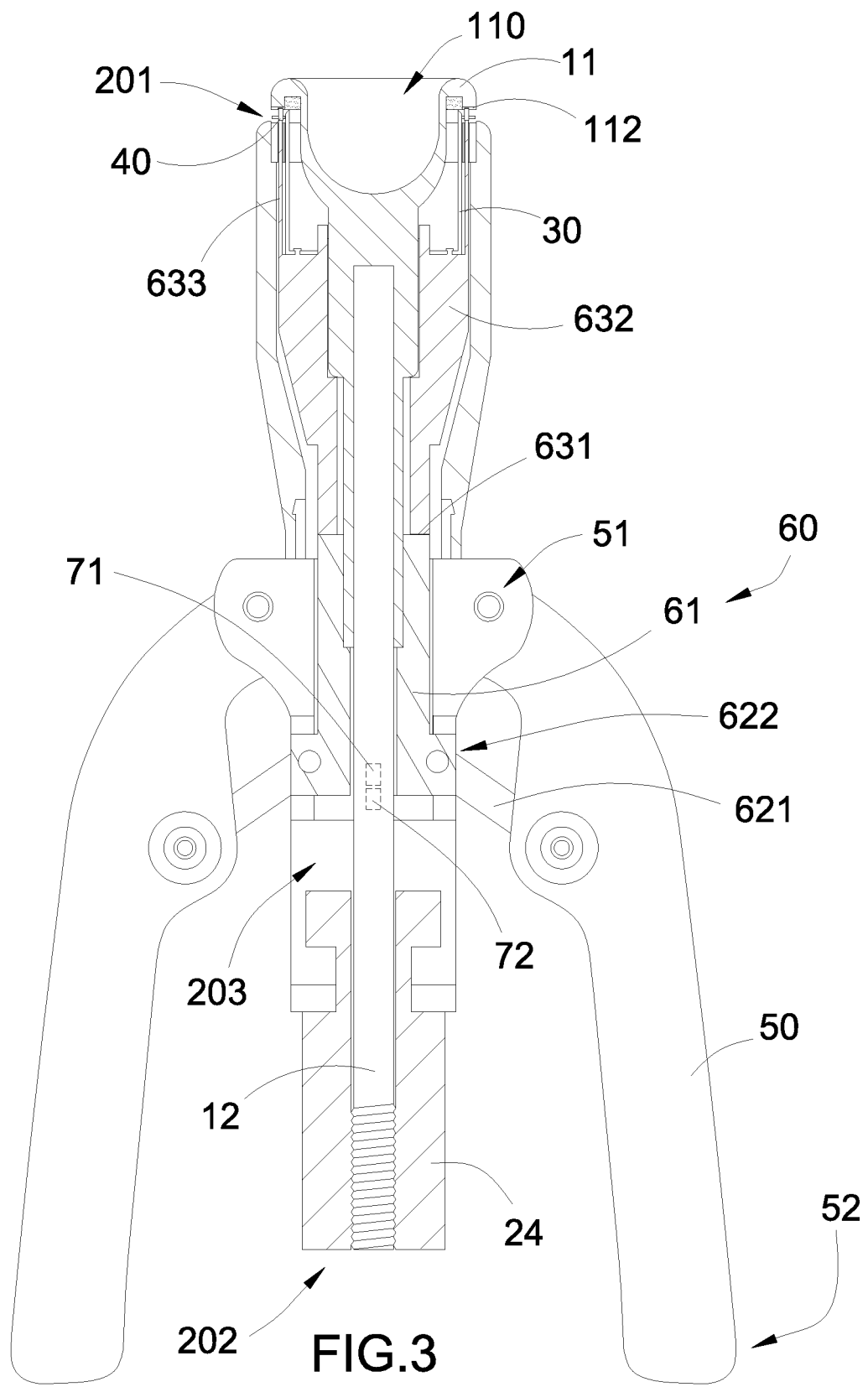
FIG. 3 is a sectional view of the device for male circumcision and suture according to the above preferred embodiment of the present invention, illustrating the one single operative motion of the operation handles.

As shown in FIGS. 1 to 3, the operation housing 20 has an enlarged front head portion and an elongated body portion which is coaxially extended therefrom, wherein the elongated body portion has a diameter size smaller than a diameter size of the enlarged front head portion. The front edge 201 of the operation housing 20 is formed at a front end of the enlarged front head portion and the rear edge 202 of the operation is formed at a rear end of the elongated body portion. In other words, the diameter size of the shaft channel 203 at the elongated body portion is smaller than a diameter size of the shaft channel 203 at the enlarged front head portion. Therefore, the excess foreskin of the patient can be received in the shaft channel 203 at the enlarged front head portion of the operation housing 20.

In addition, a length of the socket shaft 12 matches with a length of the shaft channel 203. Accordingly, the socket shaft 12 is extended through the shaft channel 203 of the operation housing 20 until a free end of the socket shaft 12 is aligned with a rear end face of the shaft channel 203 to ensure a placement of the glans receiver socket 10, as shown in FIGS. 2 and 3. It is worth mentioning that the excess foreskin of the patient must be securely clamped and sandwiched between the front edge 201 of the operation housing 20 and the guiding seat 112 of the glans socket 11. If the excess foreskin of the patient is loosely clamped to allow any unwanted movement of the excess foreskin, the excess foreskin will be cut unevenly. Therefore, the placement of the glans receiver socket 10 must be checked by the surgeon before the operation. The present invention provides the simplest way for the surgeon to check the placement of the glans receiver socket 10 by placing a finger of the surgeon to check whether the free end of the socket shaft 12 and the rear end face of the shaft channel 203 are at the same level. In other words, when the finger of the surgeon places on the rear end face of the shaft channel 203 that the finger can touch the free end of the socket shaft 12, the placement of the glans receiver socket 10 is corrected and the surgeon can start the operation.

In order to lock up the glans socket 11 at the front edge 201 of the operation housing 20 to ensure the excess foreskin of the patient to be clamped and sandwiched between the front edge 201 of the operation housing 20 and the guiding seat 112 of the glans socket 11, the operation housing 20 further comprises a locking body 24 provided thereat and releasably locked up with the socket shaft 12. As shown in FIGS. 1 to 3, the locking body 24 is rotatably coupled at the operation housing 20 to define the rear edge 202 at the locking body 24, wherein the shaft channel 203 is extended through the locking body 24 to define the rear end face of the shaft channel 203 at the locking body 24.

In one embodiment, the locking body 24 has an inner threaded structure rotatably engaging with an outer threaded structure provided at a free end portion of the socket shaft 12. In other words, the inner threaded structure is formed at a portion of the shaft channel 203 which is formed at the locking body 24. Therefore, when the socket shaft 12 is slid into the shaft channel 203, the locking body 24 is rotated to engage the inner threaded structure with the outer threaded structure of the socket shaft 12 so as to lock up the glans socket 11 at the front edge 201 of the operation housing 20 for ensuring the excess foreskin of the patient to be securely retained between the front edge 201 of the operation housing 20 and the guiding seat 112 of the glans socket 11. Therefore, when the finger of the surgeon places on the rear end face of the shaft channel 203, i.e.

the rear end of the locking body 24, the finger can touch the free end of the socket shaft 12 to ensure the corrected placement of the glans receiver socket 10. An adjustment knob 25, as an auxiliary driving tool, is provided to engage with the locking body 24 to drive the locking body 24 to rotate. In other words, when the locking body 24 is manually rotated to retain the socket shaft 12 within the shaft channel 203, the adjustment knob 25 can be coupled at the locking body 24 to further rotate the locking body 24 so as to secure the locking position of the socket shaft 12, i.e. the free end of the socket shaft 12 is aligned with a rear end face of the shaft channel 203.

According to the preferred embodiment, at least a portion of the socket shaft 12 has a non-circular configuration, wherein the shaft channel 203 has a portion corresponding to the non-circular configuration of the portion of the socket shaft 12. Therefore, after the socket shaft 12 is slid into the shaft channel 203, the locking body 24 is rotated to lock up the free end portion of the socket shaft 12. The non-circular configuration of the portion of the socket shaft 12 will prevent the rotational movement of the socket shaft 12 when the locking body 24 is rotated. In other words, the glans socket 11 will be stationary and will not be driven to rotate when the locking body 24 is rotated.

In addition, the non-circular configuration of the portion of the socket shaft 12 will also form an alignment means for aligning the socket shaft 12 to be slid into the shaft channel 203. In one embodiment, the alignment means comprises an alignment rib 121 radially protruded from the socket shaft 12 and an alignment slot 204 indented on a surrounding wall of the shaft channel 203, wherein when the socket shaft 12 is slid into the shaft channel 203, the alignment rib 121 is alignedly engaged with the alignment slot 204 to ensure a corrected alignment of the glans receiver socket 10. Preferably, two or more alignment ribs 121 are radially protruded from the socket shaft 12 and two or more corresponding alignment slots 204 are indented on the surrounding wall of the shaft channel 203. Preferably, one of the alignment ribs 121 serves as a main alignment rib which has different configurations of other alignment ribs 121. For example, the main alignment rib 121 is colored, such as black color, different from other alignment ribs 121.

The size of the main alignment rib 121 can be different from other alignment ribs 121. Preferably, the main alignment rib 121 should be towards the position of ventral or dorsal to make easier for operation when aligning with the alignment slot 204. It is worth mentioning that when the alignment rib 121 is engaged with the alignment slot 204, the glans socket 11 will be stationary and will not be driven to rotate during the rotation of the locking body 24.

Figure 4:
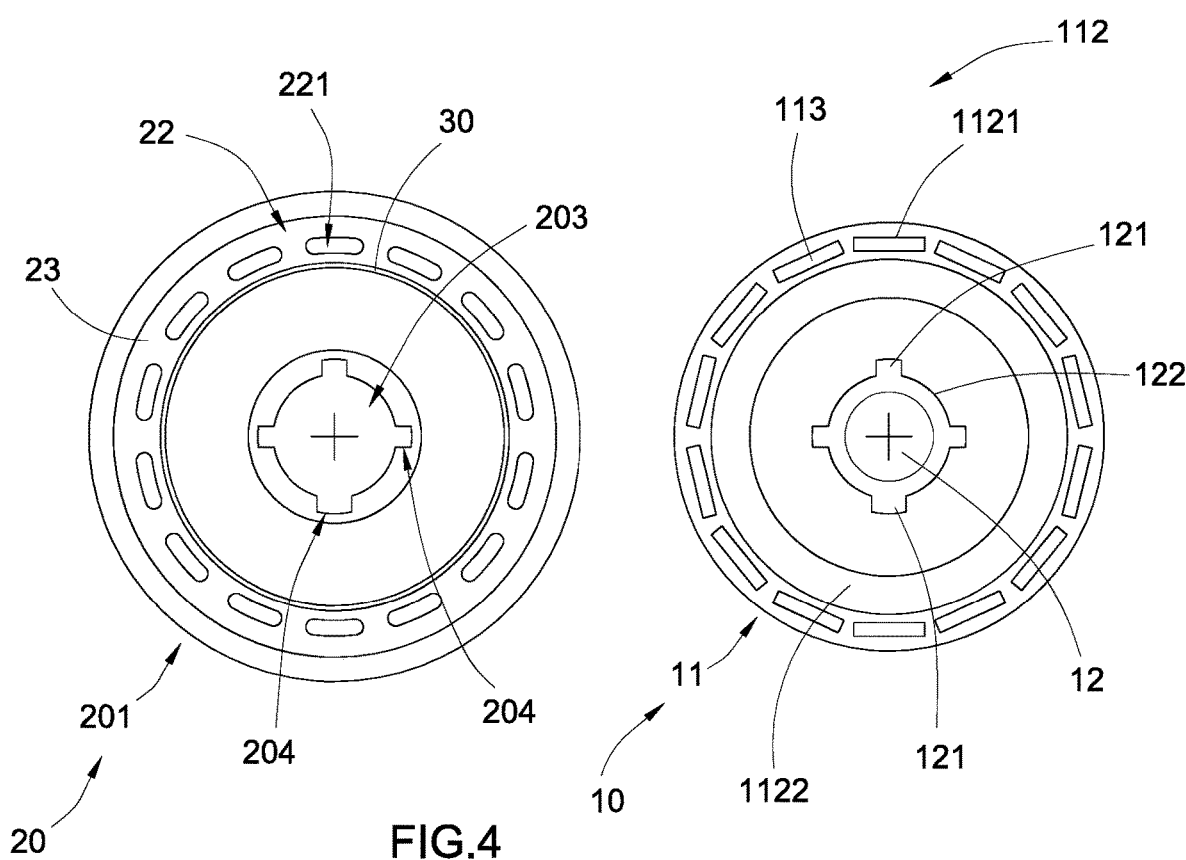
FIG. 4 is a front view of the device for male circumcision and suture according to the above preferred embodiment of the present invention, illustrating the corresponding structure between the socket shaft and the shaft channel.

As shown in FIG. 4, the alignment means comprises a tubular alignment body 122 integrally extended from the apex of the glans socket 11, wherein the socket shaft 12 is coaxially extended through the alignment body 122. The alignment ribs 121 are radially and integrally extended from the alignment body 122, such that the alignment ribs 121 are radially and outwardly projected from the socket shaft 12.

According to the preferred embodiment, the annular cutter 30 is retractably and coaxially coupled at the front edge 201 of the operation housing 20. In particular, the annular cutter 30 is received at the enlarged front head portion of the operation housing 20. The annular cutter 30 has a front cutting edge 31 coaxially received in the front edge 201 of the operation housing 20 and arranged to be pushed forward at a position that the front cutting edge 31 of the annular cutter 30 is pushed out of the front edge 201 of the operation housing 20. Therefore, after the excess foreskin of the patient will be clamped and sandwiched between the front edge 201 of the operation housing 20 and the guiding seat 112 of the glans socket 11, the front cutting edge 31 of the annular cutter 30 is pushed out of the front edge 201 of the operation housing 20 for cutting the excess foreskin of the patient. It is worth mentioning that the front cutting edge 31 of the annular cutter 30 is pushed to contact with the inner seat portion of the guiding seat 112 of the glans socket 11 for cutting the excess foreskin of the patient.

Figure 5:
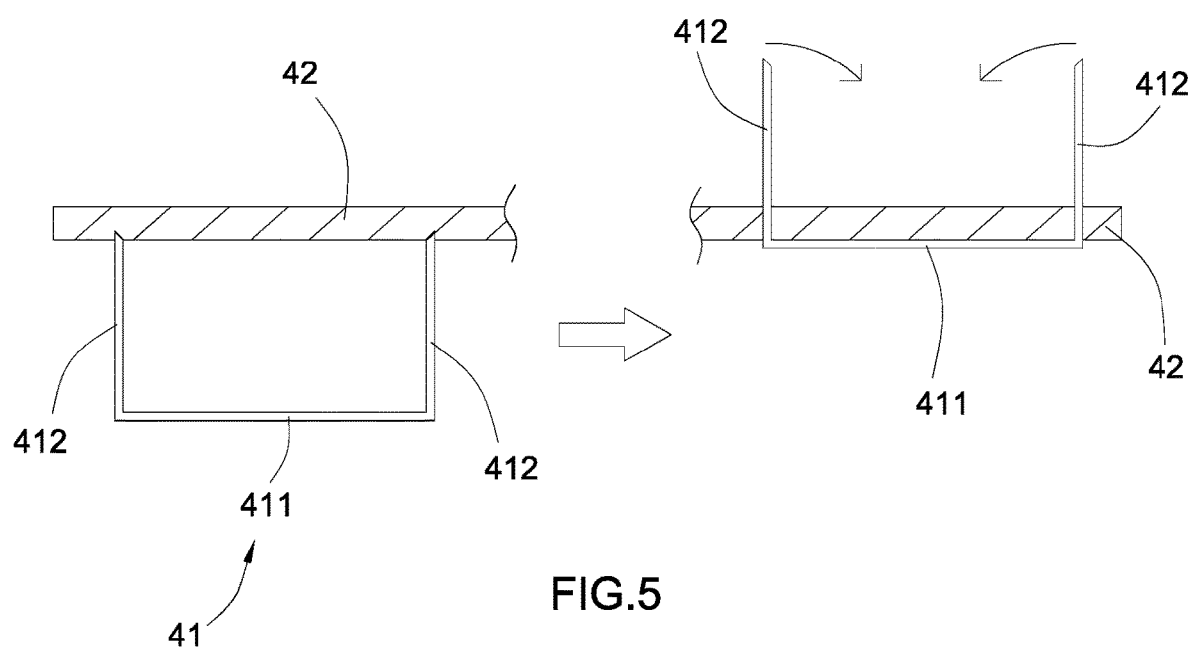
FIG. 5 illustrates the suture cartridge of the device for male circumcision and suture according to the above preferred embodiment of the present invention, showing the staple penetrating through the holding band.

The suture cartridge 40 comprises a plurality of staples 41 spacedly disposed at the front edge 201 of the operation housing 20. Accordingly, when the staples 41 are pushed out of the front edge 201 of the operation housing 20, the staples 41 are pushed to penetrate through the excess foreskin of the patient at the cut area thereof for applying the stitches to the cut area of the skin, as shown in FIG. 7. As shown in FIG. 5, each of the staples 41, having a U-shaped configuration, has a staple body 411 and two staple pins 412, wherein when the staple 41 is pushed to the guiding seat 112, the staple pins 412 are guided and bent by the staple guiding indentions 113 of the outer seat portion of the guiding seat 112 for stitching the cut area of the skin.

As shown in FIGS. 2 to 3 and 5 to 7, the suture cartridge 40 further comprises an annular holding band 42 that the staples 41 are evenly disposed therearound, such that when the holding band 42 is disposed at the front edge 201 of the operation housing 20, the staples are automatically lined up therearound. Accordingly, the staple pins 412 of each of the staples 41 are penetrated through the holding band 42, such that the staples 41 are held by the holding band 42 in a circular manner. Preferably, the holding band 42 is made of flexible material. It is worth mentioning that when the staples 41 are pushed for penetrating the staple pins 412 through the skin to stitch the cut area of the skin, the holding band 42 is correspondingly pushed to encircle around the cut area of the skin. Therefore, the holding band 42 also serves as a cushioning element to absorb any excessive penetrating force of each of the staples 41 during the stitching operation. In other words, the holding band 42 not only ensures the corrected alignment of the staples 41 to be evenly spaced apart with each other but also provides a buffering clearance between the staples 41 and the cut area of the patient so as to prevent the direct stapling contact of the staples 41 to the cut area of the patient.

According to the preferred embodiment, the device of the present invention further comprises two operation handles 50 pivotally coupled at the operation housing 20 to actuate the annular cutter 30 and the suture cartridge 40 at the same time. In particular, when the operation handles 50 are concurrently and pivotally moved toward the operation housing 20, as shown in FIG. 3, the annular cutter 30 is pushed out of the front edge 201 of the operation housing 20 to contact with the guiding seat 112 of the glans socket 11 for removing the excess foreskin of the patient and at the same time, the staples 41 are pushed to contact with the guiding seat 112 of the glans socket 11 for applying the stitches at the cut area of the excess foreskin of the patient. Therefore, the device of the present invention can precisely remove excess foreskin from the penis during circumcision via the annular cutter 30 and, at the same time, can rapidly apply stitches to the cut area of the skin via the staples 41 in one single operative motion of the operation handles 50, as shown in FIG. 7.

Accordingly, each of the operation handles 50 has a pivot end 51 pivotally coupled at an exterior wall of the operation housing 20 and a free end 52 extended toward the rear edge 202 of the operation housing 20, such that the free ends 52 of the operation handles 50 are moved toward the operation housing 20 to actuate the annular cutter 30 and the suture cartridge 40 at the same time. It is worth mentioning that each of the operation handles 50 requires a relatively short pivotal traveling path to actuate the annular cutter 30 and the suture cartridge 40 at the same time. The actuation of the operation handles 50 requires the concurrent pressing forces at the operation handles 50 toward the operation housing 20. In other words, the pressing forces must be evenly applied toward the operation housing 20 to ensure the alignment of the annular cutter 30 with the glans socket 11. Therefore, the surgeon is able to use one hand to hold the operation handles 50 and to apply a gripping force, as the pressing force, thereat to concurrently actuate the operation handles 50. Since the pressing forces at the operation handles 50 are even, the operation housing 20 will keep its original position in a stable manner to retain the corrected alignment with the excess foreskin of the patient.

As shown in FIGS. 1 to 3, the operation housing 20 further has a tubular cutter cavity 21 formed at the front edge 201 and coaxially aligned with the front opening of the shaft channel 203, wherein the annular cutter 30 is movably received at the tubular cavity 21 of the operation housing 20. Preferably, the cutter cavity 21 is formed at a periphery of the front opening of the shaft channel 203. Therefore, the front cutting edge 31 of the annular cutter 30 is pushed out of the cutter cavity 21 through the front opening of the shaft channel 203 for removing the excess foreskin of the patient. In addition, the operation of the device is simple, rapid, and easy by the single action of the operation handle 50, so as to substantially reduce the significant amount of the pain and trauma associated with the circumcision. To prevent the excessive pressing force applied on the operation handle 50, each of the operation handles 50 is made of breakable material having a safety factor to prevent the over pressing force applied on the operation handles 50. For example, the operation handle 50 will be broken if the pressing force is larger than 45 kg.

The operation housing 20 further has a retention seat 22 indently formed around the front edge 201 thereof to receive the holding band 42 within the retention seat 22. Accordingly, the retention seat 22 is an annular indention indented at the front edge 201 of the operation housing 20 and is coaxially aligned with the front opening of the shaft channel 203. In particular, the annular cutter 30 is coaxially located within the retention seat 22. In other words, the staples 41 held by the holding band 42 are disposed around the front edge 201 of the operation housing 20 at the retention seat 22 thereof to coaxially align with the annular cutter 30 at a position that the annular cutter 30 is located within the staples 41. As a result, when the excess foreskin of the patient is removed by the annular cutter 30, the cut area of the patient will be stitched by the staples 41 at the same time.

In order to form the retention seat 22 around the front edge 201 of the operation housing 20, the operation housing 20 further comprises an annular front rim member 23 coupled at the front edge of the operation housing 20, wherein the retention seat 22 is formed at the front rim member 23 to receive the holding band 42 and the staples 41 thereat.

The operation housing 20 further comprises a safety cap 26 detachably coupled at the front edge 201 of the operation housing 20 to enclose the suture cartridge 40 and the annular cutter 30. In particular, the safety cap 26 is detachably coupled at the front edge 201 of the operation housing 20 to cover the retention seat 22. Therefore, the cutting edge 31 of the annular cutter 30 and the staples 41 and the holding band 42 of the suture cartridge 40 are protected by the safety cap 26. The surgeon can remove the safety cap 26 during the operation of the present invention.

In order to actuate the annular cutter 30 and the suture cartridge 40 at the same time by the operation handles 50, the device of the present invention further comprises an actuation unit 60 for driving the annular cutter 30 and the suture cartridge 40 at the same time. As shown in FIGS. 2 and 3, the actuation unit 60 comprises a driving shaft 61 movably disposed in the operation housing 20, a driving arm unit 62 operatively linked between the operation handles 50 and the driving shaft 61 to drive the driving shaft 61 to slide within the operation housing 20, and a staple actuator 63 coupled with the driving shaft 61 for pushing the annular cutter 30 and the suture cartridge 40 at the same time.

As shown in FIGS. 2 and 3, the driving shaft 61 is slidably disposed in the shaft channel 203 of the operation housing 20 at the elongated body portion thereof, wherein the driving shaft 61 has a tubular configuration, such that the socket shaft 12 is coaxially slid to penetrate through the driving shaft 61. It is worth mentioning that when the driving shaft 61 is slid within the shaft channel 203, the socket shaft 12 is stationary because the socket shaft 12 is locked by the locking body 24.

The driving arm unit 62 comprises two actuating arms 621 pivotally coupled between the operation handles 50 and the driving shaft 61. In particular, two communication slots 622 are formed at the exterior wall of the operation housing 20 to communicate with the shaft channel 203. Each of the actuating arms 621 has one end pivotally coupled to the corresponding operation handle 50 and an opposed end extended to pivotally couple to the driving shaft 61 through the corresponding communication slot 622. In other words, the outer end of the actuating arm 621 is extended out of the shaft channel 203 to pivotally couple with the operation handle 50 while the inner end of the actuating arm 621 is extended into the shaft channel 203 to pivotally couple with the driving shaft 61. Therefore, when the outer ends of the operation handles 50 are pivotally moved toward the operation housing 20, the actuating arms 621 are pivotally moved to push the driving shaft 61 within the shaft channel 203 and toward the front edge 201 of the operation housing 20. It is worth mentioning that when the operation handles 50 are pivotally moved away from the operation housing 20, the actuating arms 621 are pivotally moved to pull the driving shaft 61 toward the rear edge 202 of the operation housing 20, such that the driving shaft 61 is moved within the shaft channel 203 in a reciprocating manner.

According to the preferred embodiment, the staple actuator 63 is frontwardly extended from the driving shaft 61. The staple actuator 63 is movably disposed at the enlarged front head portion of the operation housing 20 and is driven to move by the driving shaft 61, wherein the staple actuator 63 has a basin shape defining a bottom actuating wall 631 and a tubular surrounding wall 632 extended from the bottom actuating wall 631 toward the front edge 201 of the operation housing 20. As shown in FIG. 6, the annular cutter 30 is received in the staple actuator 63, wherein the driving shaft 61 is moved to push the staple actuator 63 at the bottom actuating wall 631 thereof, so as to push the tubular surrounding wall 632 and the annular cutter 30 toward the front edge 201 of the operation housing 20.

Accordingly, the staple actuator 63 further comprises a plurality of staple pusher arms 633 integrally extended from a front rim of the tubular surrounding wall 632 and movably coupled at the front edge 201 of the operation housing 20 for pushing the staples 41 to the guiding seat 112 of the glans socket 11. The staple pusher arms 633 are evenly and frontwardly protruded from the front rim of the tubular surrounding wall 632 to align with the staples 41. Therefore, the staple pusher arms 633 are actuated by the operation handles 50 via the driving shaft 61 and pushed out of the front edge 201 of the operation housing 20 so as to push the staples 41 to the guiding seat 112 of the glans socket 11 for applying the stitches at the cut area of the patient. In order to guide to staple pusher arms 633 to align with the staples 41, the operation housing 20 further has a plurality of arm guiding slots 221 formed at the retention seat 22, wherein the staple pusher arms 633 are slidably engaged with the arm guiding slots 221 respectively. In particular, the arm guiding slots 221 are through slots formed at the front rim member 23, such that when the staple pusher arms 633 are pushed out of the retention seat 22, the staples 41 at the retention seat 22 are pushed toward the guiding seat 112 of the glans socket 11. It is worth mentioning that the staples 41 are disposed in the guiding slots 221 respectively while the holding band 42 is disposed on the retention seat 22, such that when the staples 41 are pushed out of the front edge 201 of the operation housing 20, the staple pins 412 of each of the staples 41 penetrate through the holding band 42 to the guiding seat 112 of the glans socket 11 for applying the stitches at the cut area of the patient. Preferably, when the staples 41 are disposed in the guiding slots 221 respectively, sharp ends of the staples pins 412 are slightly penetrated into the holding band 42 to retain the holding band 42 on the retention seat 22, as shown in FIGS. 5 and 6. On the other hand, the staples 41 are held by the holding band 42 in a circular manner.

As it is mentioned above, the driving shaft 61 is moved within the shaft channel 203 in a reciprocating manner by the pivotal movements of the operation handles 50. However, the staple actuator 63 will only moved toward the front edge 201 of the operation housing 20 when the operation handles 50 are pivotally moved toward the operation housing 20. In other words, when the operation handles 50 are pivotally moved toward the operation housing 20, the staple actuator 63 and the annular cutter 30 will be pushed toward the front edge 201 of the operation housing 20. When the operation handles 50 are pivotally moved away from the operation housing 20, the staple actuator 63 and the annular cutter 30 will not move back to their original positions. Therefore, the device of the present invention will only allow the surgeon to operate once. In other words, the device of the present invention is a one-time use device that once the cutting edge 31 of the annular cutter 30 is pushed out of the front edge 201 of the operation housing 20 for removing the excess foreskin of the patient, the cutting edge 31 of the annular cutter 30 cannot be retracted back into the front edge 201 of the operation housing 20 by the operation handles 50 for safety purpose. It is because when the cutting edge 31 of the annular cutter 30 is pushed out of the front edge 201 of the operation housing 20, the excess foreskin of the patient is removed by the first time cut. If the annular cutter 30 can be retracted by the operation handles 50, the annular cutter 30 may accidentally pushed again to cut the foreskin at the second time.

Accordingly, the device of the present invention further comprises a locking mechanism 70 for releasably locking the pivotal movements of the operation handles 50, as shown in FIGS. 1 to 3. The locking mechanism 70 comprises a first locking slot 71 formed on the driving shaft 61, a second locking slot 72 formed on the operation housing 20, and a locker member 73 detachably engaging with the first and second locking slots 71, 72 when the driving shaft 61 is slid within the shaft channel 203 to align the first locking slot 71 with the second locking slot 72. The locker member 73 has an inserting portion arranged to detachably insert into the first locking slot 71 through the second locking slot 72 to lock up the sliding movement of the driving shaft 61. It is worth mentioning that when the driving shaft 61 is locked within the shaft channel 203, the operation handles 50 cannot be pivotally moved toward the operation housing 20. In addition, the cutting edge 31 of the annular cutter 30 and the staples 41 cannot be pushed out of the front edge 201 of the operation housing 20 via the driving shaft 61. The surgeon can remove the locker member 73 to disengage with the first and second locking slots 71, 72 to unlock the sliding movement of the driving shaft 61 so as to enable the pivotal movements of the operation handles 50.

According to the preferred embodiment, the present invention further provides a method for manufacturing the device for male circumcision and suture, which comprises the following steps.

(1) Form the glans receiver socket 10 to have the glans socket 11 having the guiding seat 112, and the socket shaft extended from the glans socket 11.

(2) Form the operation housing 20 to have the shaft channel 203 extended from the front edge 201 to the rear edge 202.

(3) Coaxially couple the annular cutter 30 at the front edge 201 of the operation housing 20.

(4) Dispose the suture cartridge 40 which has the staples 41 at the front edge 201 of the operation housing 20.

(5) Slidably pass the socket shaft 12 through the shaft channel 203 until the front edge 201 of the operation housing 20 is biased against the guiding seat 112 of the glans socket 11, so as to detachably couple the glans receiver socket 10 with the operating housing 20.

(6) Pivotally couple two operation handles 50 at the operation housing 20 to actuate the annular cutter 30 and the suture cartridge 40 at the same time, wherein when the operation handles 50 are concurrently and pivotally moved towards the operation housing 20, the cutting edge 31 of the annular cutter 30 is pushed out of the front edge 201 of the operation housing 20 to contact with the guiding seat 112 of the glans socket 11 for removing the excess foreskin of the patient and at the same time, the staples 41 are pushed to contact with the guiding seat 112 of the glans socket 11 for applying stitches at the cut area of the excess foreskin of the patient.

In order to assemble the device male circumcision and suture, the present invention further provides an assembling method which comprises the following steps.

(I) Dispose the suture cartridge 40 at the front edge 201 of the operation housing 20. Accordingly, the suture cartridge 40 is pre-installed at the front edge 201 of the operation housing 20 by disposing the holding band 42 with the staples 41 at the retention seat 22.

(II) Cover the safety cap 26 at the front edge 201 of the operation housing 20 to enclose the suture cartridge 40 and the cutting edge 31 of the annular cutter 30. Accordingly, the suture cartridge 40 and the cutting edge 31 of the annular cutter 30 are already sterilized, such that the safety cap 26 can prevent any germ entering to the suture cartridge 40 and the annular cutter 30.

(III) Slidably insert the socket shaft 12 of the glans receiver socket 10 into the shaft channel 203 of the operation housing 20 until the glans socket 11 of the glans receiver socket 10 is biased against the front edge 201 of the operation housing 20 to retain the safety cap 26 between the glans socket 11 and the front edge 201 of the operation housing 20. Once the safety cap 26 is sandwiched between the glans socket 11 and the front edge 201 of the operation housing 20, the safety cap 26 cannot be removed without detaching the glans receiver socket 10 from the operation housing 20 so as to prevent any touch of the suture cartridge 40 and the annular cutter 30 before the usage.

(IV) Seal and pack the operation housing 20 with the glans receiver socket 10 in a disinfected package. Therefore, the device of the present invention is ready to use by removing the device from the disinfected package.

According to the preferred embodiment, the present invention further provides an operating method for male circumcision and suture, comprising the following steps.

(A) Provide the glans receiver socket 10. Accordingly, a glans size template is used to measure the glans by inserting the glans into the plate at the middle or two-thirds of the position. It should begin by selecting a little tight hole is better. Then, the appropriate size of the glans receiver socket 10 is selected. Therefore, the device can be unpacked from the disinfected package and the glans receiver socket 10 can be detached from the operation housing 20.

(B) Insert the glans socket 11 of the glans receiver socket 10 into the excess foreskin of the patient to cover the glans thereof. The glans receiver socket 10 must be sterilized before inserting into the excess foreskin of the patient. Patients with phimosis are required to make an incision of the dorsal to create a viable surgical length until the glans receiver socket 10 can insert in it.

(C) Slide the socket shaft 12 into the shaft channel 203 of the operation housing 20 until the front edge 201 of the operation housing 20 biased against the guiding seat 112 of the glans socket 11 for retaining the excess foreskin of the patient between the front edge 201 of the operation housing 20 and the guiding seat 112 of the glans socket 11. It is worth mentioning that the glans receiver socket 10 should not be pulled from the glans of the patient to avoid incorrect cutting after the foreskin slides down. Accordingly, when the socket shaft 12 is slid into the shaft channel 203, the alignment rib 121 is alignedly engaged with the alignment slot 204 to ensure a corrected alignment of the glans receiver socket 10.

It is worth mentioning that before the socket shaft 12 is slid into the shaft channel 203, the safety cap 26 should be removed from the front edge 201 of the operation housing 20 to expose the suture cartridge 40 and the annular cutter 30.

(D) Secure the socket shaft 12 at the shaft channel 203 to lock up the glans socket 11 at the front edge 201 of the operation housing 20. The surgeon is able to rotate the locking body 24 to engage the inner threaded structure with the outer threaded structure of the socket shaft 12 so as to lock up the glans socket 11 at the front edge 201 of the operation housing 20 for ensuring the excess foreskin of the patient to be securely retained between the front edge 201 of the operation housing 20 and the guiding seat 112 of the glans socket 11. The adjustment knob 25 can be used to engage with the locking body 24 and to drive the locking body 24 to rotate until the free end of the socket shaft 12 is aligned with a rear end face of the shaft channel 203.

Once the glans socket 11 is locked at the front edge 201 of the operation housing 20, the locker member 73 can be detached from the operation housing 20 to disengage with the first and second locking slots 71, 72. Therefore, the operation handles 50 are now free to pivotally move to drive the driving shaft 61 to slide within the shaft channel 203.

(E) Pivotally actuate two operation handles 50 at the operation housing 20 to actuate the annular cutter 30 and the suture cartridge 40 at the same time. Accordingly, the surgeon is able to apply a squeezing force, i.e. the pressing force, at the operation handles 50 at the same time in one single operative motion to actuate the annular cutter 30 and the suture cartridge 40 at the same time. The step (E) further comprises the following steps.

(E.1) Push the cutting edge 31 of the annular cutter 30 out of the front edge 201 of the operation housing 20 to contact with the guiding seat 112 of the glans socket 11 for removing the excess foreskin of the patient.

(E.2) Push the staples 41 of said suture cartridge 40 to contact with the guiding seat 112 of the glans socket 11 for applying stitches at the cut area of the excess foreskin of the patient. Accordingly, the staples 41 are linked by the holding band 42 and are pre-installed at the front edge 201 of the operation housing.

Accordingly, when the operation handles 50 are pressed, the driving shaft 61 is moved by the actuating arms 621 to push the staple actuator 63 toward the front edge 201 of the operation housing 20. As a result, the cutting edge 31 of the annular cutter 30 and the staples 41 are pushed out of the front edge 201 of the operation housing 20 at the same time. The excess foreskin of the patient is cut by the annular cutter 30 and at the same time, the cut area of the patient is stitched by the staples 41.

(F) Unlock the socket shaft 12 from the shaft channel 203 of the operation housing 20. The surgeon is able to use the adjustment knob 25 to drive the locking body 24 to rotate in order to initially unlock the socket shaft 12 from the shaft channel 203. Then, the locking body 24 can be rotated by hand to release the socket shaft 12 from the shaft channel 203.

(G) Slide the socket shaft 12 out of the front edge 201 of the operation housing 20 to detach the glans receiver socket 10 from the operation housing 20. It is worth mentioning that the cut excess foreskin of the patient will remain either in the enlarged front head portion of the operation housing 20 or at the conical surface of the glans socket 11 when the glans receiver socket 10 is detached from the operation housing 20.

(H) Cut the holding band 42 between two of the staples 41 while keeping the staples 41 in position. It is worth mentioning that when the staples 41 are pushed for stitching the cut area of the patient, the holding band 42 is correspondingly pushed to encircle around the cut area of the patient. Therefore, a clearance of the holding band 42 between the staples 41 should be cut to release the pressure on the cut area of the patient from the holding band 42. Then, the cut area of the patient can be wrapped by sterilized gauze.

It is worth mentioning that after the operation is completed, the safety cap 26 can be placed back to the front edge 201 of the operation housing 20 to retract the cutting edge 31 of the annular cutter 30 back to the front edge 201 of the operation housing 20 by pushing back thereto. The safety cap 26 can also prevent the used annular cutter 30 from being contacted. Then, the glans receiver socket 10 can be coupled back to the operation housing 20 by sliding the socket shaft 12 to the shaft channel 203 and locking the socket shaft 12 by the locking body 24.

Figure 8:
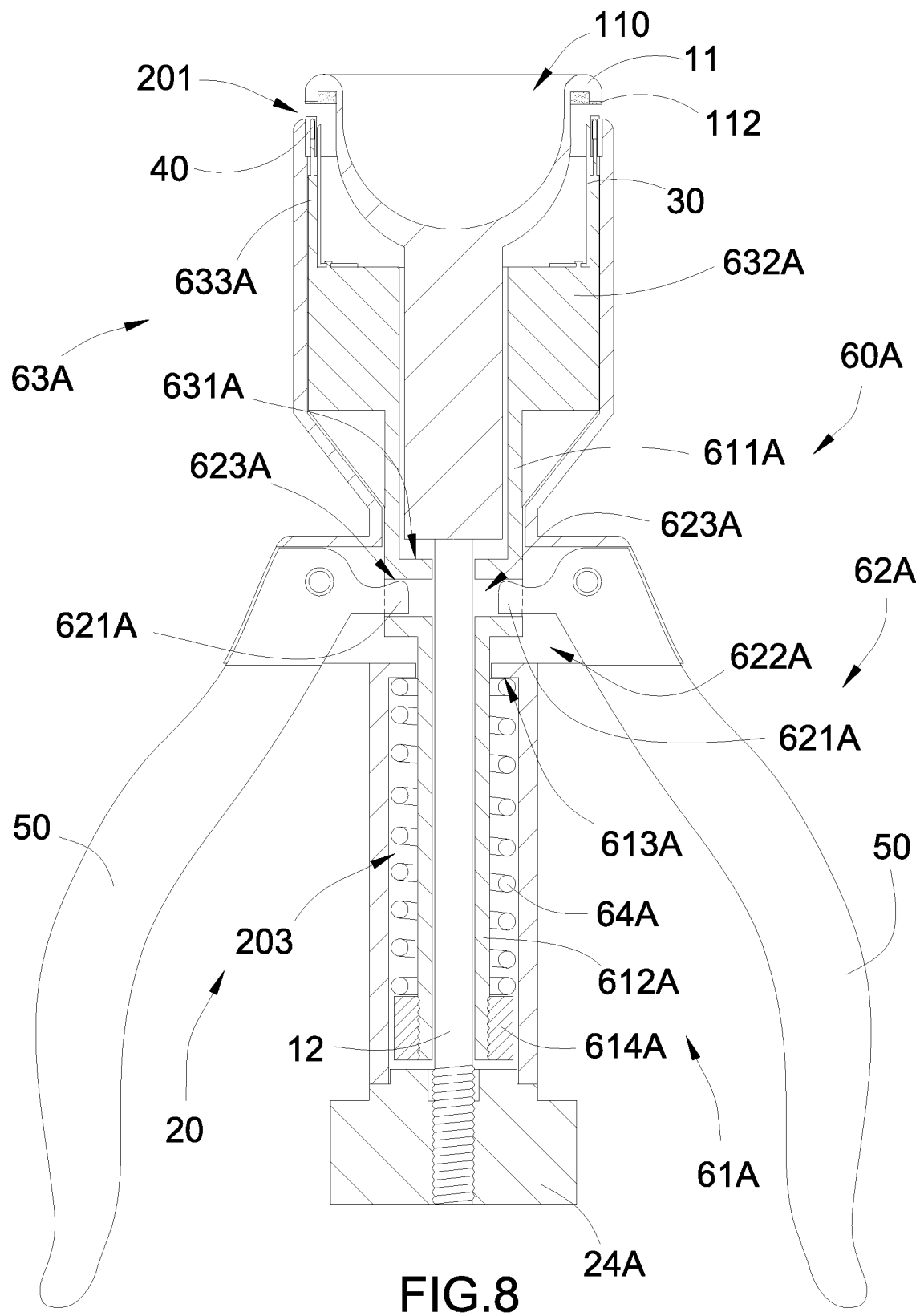
FIG. 8 is a sectional view of the device for male circumcision and suture according to a second preferred embodiment of the present invention.
Figure 9:
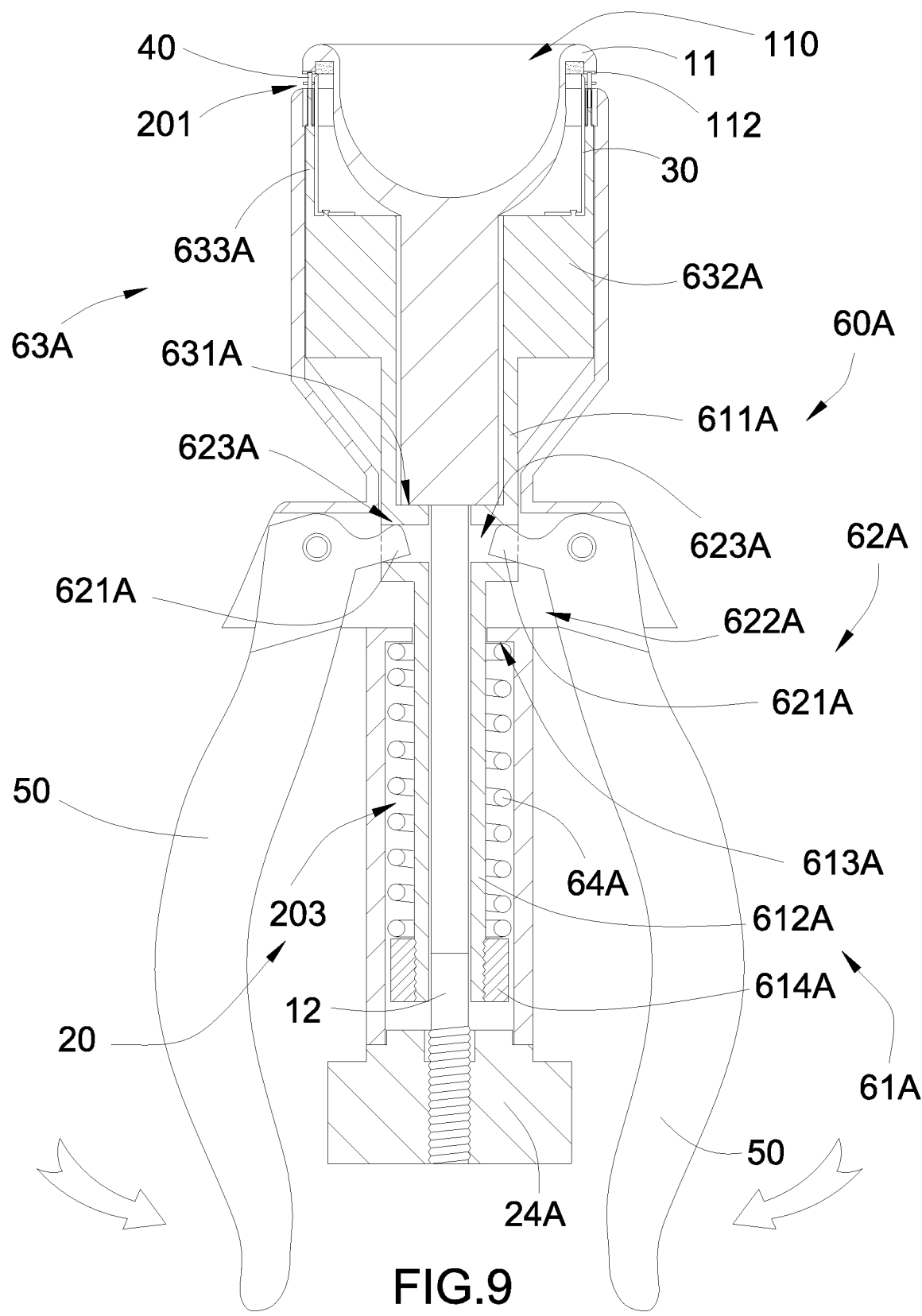
FIG. 9 is a sectional view of the device for male circumcision and suture according to the above second preferred embodiment of the present invention, illustrating the one single operative motion of the operation handles.

As shown in FIGS. 8 and 9, a device for male circumcision and suture according to a second embodiment illustrates an alternative mode of the first embodiment, wherein the structural configuration of the first embodiment is the same as that of the second embodiment, except the actuation unit 60A. Accordingly, the actuation unit 60A is actuated for driving the annular cutter 30 and the suture cartridge 40 at the same time. The actuation unit 60A comprises a driving shaft 61A movably disposed in the operation housing 20, a driving arm unit 62A operatively linked between the operation handles 50 and the driving shaft 61A to drive the driving shaft 61A to slide within the operation housing 20, and a staple actuator 63A coupled with the driving shaft 61A for pushing the annular cutter 30 and the suture cartridge 40 at the same time. The actuation unit 60A further comprises a resilient element 64A biased against the driving shaft 61A to push the staple actuator 63A away from the annular cutter 30 and the suture cartridge 40. The resilient element 64A will apply a resilient force against the driving shaft 61A to prevent the pivotal actuation of each of the operation handles 50. In other words, the operator must actuate the operation handles 50 to overcome the resilient force of the resilient element 64A in order to operate the male circumcision and suture for driving the annular cutter 30 and the suture cartridge 40 at the same time.

Accordingly, the driving shaft 61A is slidably disposed in the shaft channel 203 of the operation housing 20, wherein the driving shaft 61A has a tubular configuration, such that the socket shaft 12 is coaxially slid to penetrate through the driving shaft 61A. The driving shaft 61A has a tubular shaft body 611A and an elongated narrow tail body 612A rearwardly extended from the shaft body 611A towards a rear end of the shaft channel 203, wherein the resilient element 64A is coaxially coupled at the narrow tail body 612A of the driving shaft 61A. An outer diameter of the shaft body 611A is larger than an outer diameter of the narrow tail body 612A. In other words, the resilient element 64A is coaxially coupled at the narrow tail body 611A of the driving shaft 61A.

As shown in FIGS. 8 and 9, the resilient element 64A is a compression spring, wherein the narrow tail body 612A is coaxially and slidably into the resilient element 64A. An inner diameter of the resilient element 64A is larger than the outer diameter of the narrow tail body 612A. Accordingly, a stopper shoulder 613A is inwardly protruded from an inner circumferential wall of the shaft channel 203 of the operation housing 20.

In particular, the length of the resilient element 64A between two ends thereof is longer than the length of the narrow tail body 612A. Accordingly, the driving shaft 61A further comprises a shaft stopper 614A, preferably having a ring shape, coupled at an end portion of the narrow tail body 612A. In one embodiment, the end portion of the narrow tail body 612A has an outer threaded portion to detachably couple with an inner threaded portion of the shaft stopper 614A. Therefore, the resilient element 64A is held at the narrow tail body 612A. In other words, one end of the resilient element 64A is biased against the stopper shoulder 613A and an opposed end of the resilient element 64A is biased against the shaft stopper 614A, such that the resilient element 64A will apply a resilient force at the driving shaft 61A to push the driving shaft 61A rearwardly.

The driving arm unit 62A comprises two actuating arms 621A integrally extended from two inner ends of the operation handles 50 to pivotally couple at the driving shaft 61A. In particular, two communication slots 622A formed at the exterior wall of the operation housing 20 to communicate with the shaft channel 203. In particular, the driving arm unit 62A further has two actuating slots 623A indentedly formed at the shaft body 611A, wherein the inner end of the actuating arm 621A is extended into the shaft channel 203 to engage with the actuating slot 623A.

Each of the actuating arms 621A has a hook end to engage with the actuating slot 623A to drive the driving shaft 61A to move forwardly within the shaft channel 203. The hook end of each of the actuating arms 621A is extended to couple to the driving shaft 61A through the corresponding communication slot 622A. In other words, the inner end of the actuating arm 621A is extended into the shaft channel 203 to engage with the actuating slot 623A at the driving shaft 61A. Preferably, the hook end of each of the actuating arms 621A is pointing forward to push the driving shaft 61A forward along the shaft channel 203.

Therefore, when the outer ends of the operation handles 50 are pivotally moved toward the operation housing 20, the actuating arms 621A are pivotally moved to push the driving shaft 61A within the shaft channel 203 and toward the front edge 201 of the operation housing 20. It is worth mentioning that when the operation handles 50 are pivotally moved away from the operation housing 20, the actuating arms 621A are pivotally moved to pull the driving shaft 61A toward the rear edge 202 of the operation housing 20, such that the driving shaft 61A is moved within the shaft channel 203 in a reciprocating manner.

Preferably, the resilient element 64A is compressed at its pre-compressed state and held between the stopper shoulder 613A and the shaft stopper 614A, as shown in FIG. 8, such that resilient force, i.e. the spring force, of the resilient element 64A not only applies to the driving shaft 61A to move rearwardly but also to push the operation handles 50 to be pivotally moved away from the operation housing 20. Therefore, when the outer ends of the operation handles 50 are pivotally moved toward the operation housing 20 via a squeezing force of the operator's hand for operation, the driving shaft 61A is driven to move forwardly to further compress the resilient element 64A to its further compressed state, as shown in FIG. 9. Once the squeezing force is released from the operation handles 50, the compressed resilient element 64A will return back to its original form at its pre-compressed state to push the operation handles 50 to be pivotally moved away from the operation housing 20. It is worth mentioning that the resilient element 64A is pre-compressed to push the operation handles 50 at their outward extending positions. The pre-compressed resilient element 64A will prevent any unwanted pivotal moving clearance of each of the operation handles 50. The operator must apply the gripping force at the operation handles 50 to overcome the resilient force of the resilient element 64A from its pre-compressed state to its further compressed state in order to pivotally move the operation handles 50 from the outward extending positions to the inward pressing positions for completing the operation.

According to the preferred embodiment, the staple actuator 63A is integrally and frontwardly extended from the driving shaft 61A. The staple actuator 63A is movably disposed at the enlarged front head portion of the operation housing 20 and is driven to move by the driving shaft 61A, wherein the staple actuator 63A has a basin shape defining a bottom actuating wall 631A and a tubular surrounding wall 632A extended from the bottom actuating wall 631A toward the front edge 201 of the operation housing 20. Preferably, the bottom actuating wall 631A is integrally and frontwardly extended from the driving shaft 61A. In other words, the driving shaft 61A and the staple actuator 63A are integrated to form an elongated single tubular body. As shown in FIG. 8, the annular cutter 30 is received in the staple actuator 63A, wherein the driving shaft 61A is moved to push the staple actuator 63A at the bottom actuating wall 631A thereof, so as to push the tubular surrounding wall 632A and the annular cutter 30 toward the front edge 201 of the operation housing 20.

Accordingly, the staple actuator 63A further comprises a plurality of staple pusher arms 633A integrally extended from a front rim of the tubular surrounding wall 632A and movably coupled at the front edge 201 of the operation housing 20 for pushing the staples 41 to the guiding seat 112 of the glans socket 11. The staple pusher arms 633A are evenly and frontwardly protruded from the front rim of the tubular surrounding wall 632A to align with the staples 41. Therefore, the staple pusher arms 633A are actuated by the operation handles 50 via the driving shaft 61A and pushed out of the front edge 201 of the operation housing 20 so as to push the staples 41 to the guiding seat 112 of the glans socket 11 for applying the stitches at the cut area of the patient. In order to guide to staple pusher arms 633A to align with the staples 41, the operation housing 20 further has a plurality of arm guiding slots 221 formed at the retention seat 22, wherein the staple pusher arms 633A are slidably engaged with the arm guiding slots 221 respectively. In particular, the arm guiding slots 221 are through slots formed at the front rim member 23, such that when the staple pusher arms 633A are pushed out of the retention seat 22, the staples 41 at the retention seat 22 are pushed toward the guiding seat 112 of the glans socket 11. It is worth mentioning that the staples 41 are disposed in the guiding slots 221 respectively while the holding band 42 is disposed on the retention seat 22, such that when the staples 41 are pushed out of the front edge 201 of the operation housing 20, the staple pins 412 of each of the staples 41 penetrate through the holding band 42 to the guiding seat 112 of the glans socket 11 for applying the stitches at the cut area of the patient. Preferably, when the staples 41 are disposed in the guiding slots 221 respectively, sharp ends of the staples pins 412 are slightly penetrated into the holding band 42 to retain the holding band 42 on the retention seat 22. On the other hand, the staples 41 are held by the holding band 42 in a circular manner.

It is appreciated that by incorporating the resilient element 64A within the shaft channel 203 to push the driving shaft 61A rearward, the annular cutter 30 and the suture cartridge 40 will not be actuated accidentally. The operator must intentionally apply the squeezing force at the operation handles 50 in order to overcome the resilient force of the resilient element 64A and to push the driving shaft 61A forward so as to actuate the annular cutter 30 and the suture cartridge 40 at the same time. In addition, the length of the operation housing 20 can be substantially shortened via the resilient element 64A. The resilient element 64A will also ensure the operation handles 50 to be concurrently and pivotally moved towards or away the operation housing 20, so as to a stable movement of the annular cutter 30. Moreover, the operator can easily control the squeezing force at the operation handles 50 via the resilient force of the resilient element 64A in order to control the pivotal movements of the operation handles 50 during the operation.

It is worth mentioning that once the operation is completed, i.e. the cutting edge 31 of the annular cutter 30 and the staples 41 are pushed out of the front edge 201 of the operation housing 20 at the same time, for removing the excess foreskin, the squeezing force at the operation handles 50 can be released. Once the squeezing force at the operation handles 50 is released, the resilient element 64A will automatically push the driving shaft 61A rearward so as to move the annular cutter 30 back to its original position that the cutting edge 31 of the annular cutter 30 is moved back into the front edge 201 of the operation housing 20. Accordingly, the cut area of the patient is stitched by the staples 41. In other words, the cutting edge 31 of the annular cutter 30 can be automatically retracted back to the front edge 201 of the operation housing 20 by the resilient element 64A.

Furthermore, the locking body 24A can be modified as a hand screw, wherein the operator is able to actuate the locking body 24A by hand in a tool-less manner to engage the inner threaded structure of the locking body 24A with the outer threaded structure of the socket shaft 12 so as to lock up the glans socket 11 at the front edge 201 of the operation housing 20 for ensuring the excess foreskin of the patient to be securely retained between the front edge 201 of the operation housing 20 and the guiding seat 112 of the glans socket 11.

Figure 10:
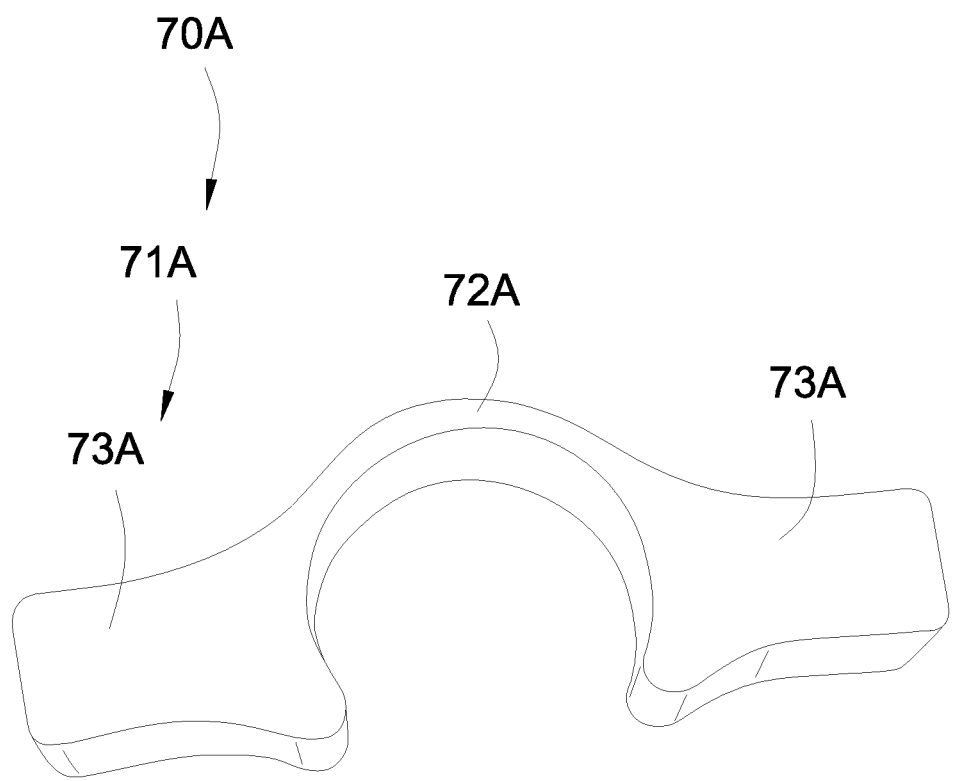
FIG. 10 is a perspective view of the locking mechanism of the device for male circumcision and suture according to the above second preferred embodiment of the present invention.
Figure 11:
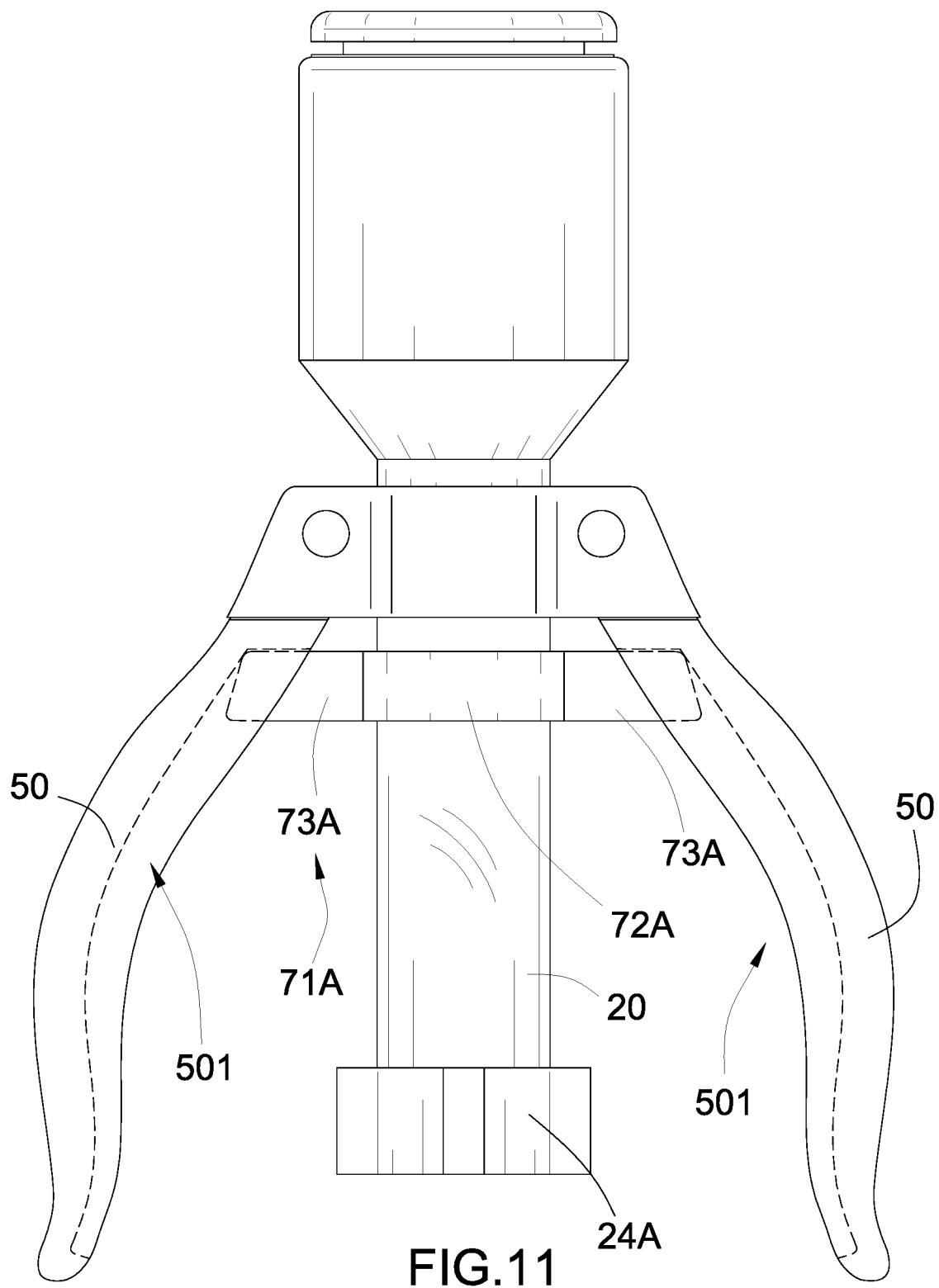
FIG. 11 illustrates the locking mechanism coupled at the operation housing for releasably locking the pivotal movements of the operation handles according to the above second preferred embodiment of the present invention.

FIGS. 10 and 11 further illustrates an alternative mode of the locking mechanism 70A for releasably locking the pivotal movements of the operation handles 50, wherein the locking mechanism 70A comprises a detachable locker 71A having a retention portion 72A detachably coupled at the operation housing 20 and two wing portions 73A sidewardly extended from the retention portion 72A to bias against the operation handles 50 respectively, so as to prevent the operation handles 50 being pivotally moved towards the operation housing 20. In other words, the pivotal movements of the operation handles 50 are locked by the detachable locker 71A.

Preferably, the retention portion 72A of the detachable locker 71A has a C-shaped cross section that the retention portion 72A is encircled around the outer circumferential surface of the operation housing 20, wherein each of the wing portions 73A has a predetermined length to bias against the corresponding operation handle 50. It is worth mentioning that the retention portion 72A can be slid along the operation housing 20 until the outer free ends of the wing portions 73A bias against the operation handles 50 respectively as shown in FIG. 11. Preferably, each of the operation handles 50 has an inner groove 501 formed at an inner side of the operation handle 50, wherein the outer free ends of the wing portions 73A are slid along the inner grooves 501 to bias against the operation handles 50. In order to detach the detachable locker 71A from the operation housing 20, the retention portion 72A can be downwardly slid along the operation housing 20 until the outer free ends of the wing portions 73A are disengaged with the operation handles 50, such that the retention portion 72A can be detached from the operation housing 20 for the operation.

It is worth mentioning that the device of the present invention can precisely determine the amount of excess foreskin to be removed from the penis of the patient by inserting the glans socket 11 of the glans receiver socket 10 into the excess foreskin of the patient and by the thickness of the front rim 111 of the glans socket 11. The device of the present invention can also precisely retain the excess foreskin between the front edge 201 of the operation housing 20 and the guiding seat 112 of the glans socket 11 to ensure the excess foreskin to be removed. By one single operation motion of the operation handles 50, the excess foreskin from the penis can be removed via the cutting edge 31 of the annular cutter 30 during circumcision and, at the same time, the cut area of the skin can be rapidly applied stitches via the staples 41 so as to substantially reduce the significant amount of the pain and trauma associated with the circumcision. The actuation of the annular cutter 30 will ensure an even incision of the excess foreskin. It is worth mentioning that the glans of the patient is covered by the glans socket 11 during the entire operation to protect the glans of the patient.

Figure 12:
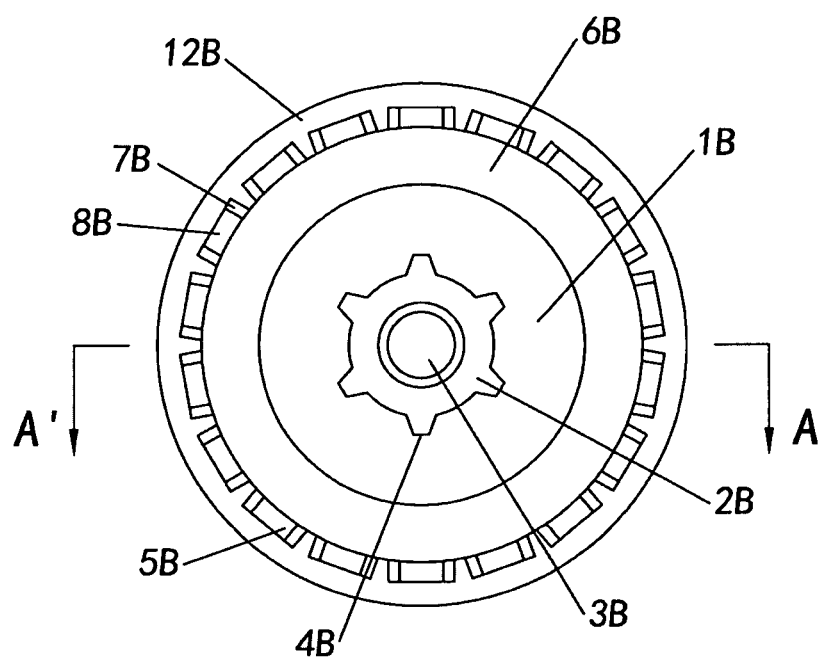
FIG. 12 is a top view of the device for male circumcision and suture according to a third preferred embodiment of the present invention.
Figure 13:
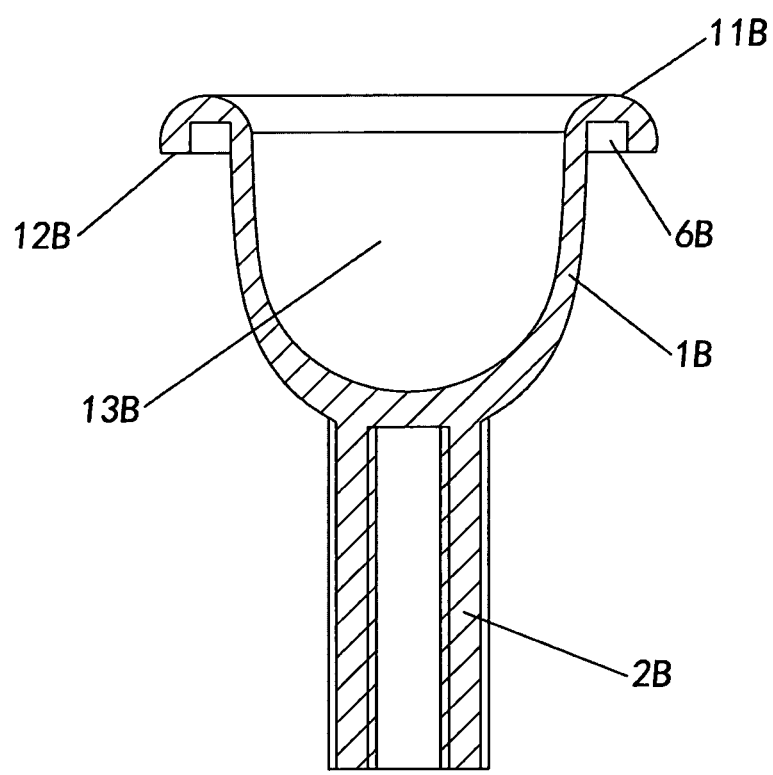
FIG. 13 is a sectional view of the glans socket and the socket shaft according to the above third preferred embodiment of the present invention.
Figure 15:
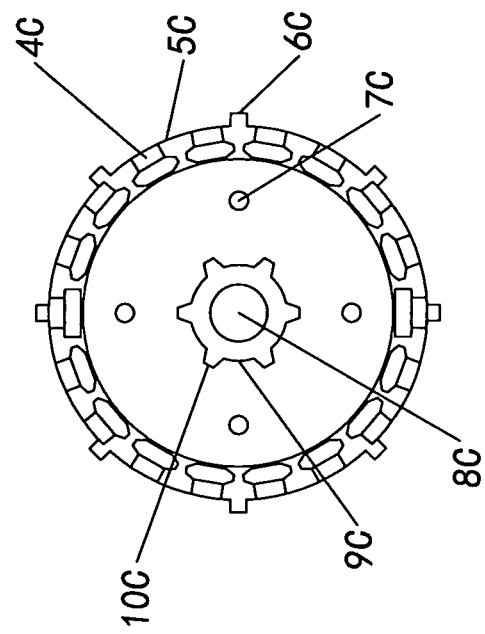
FIG. 15 is a top view of the fourth preferred embodiment of the present invention.
Figure 14:
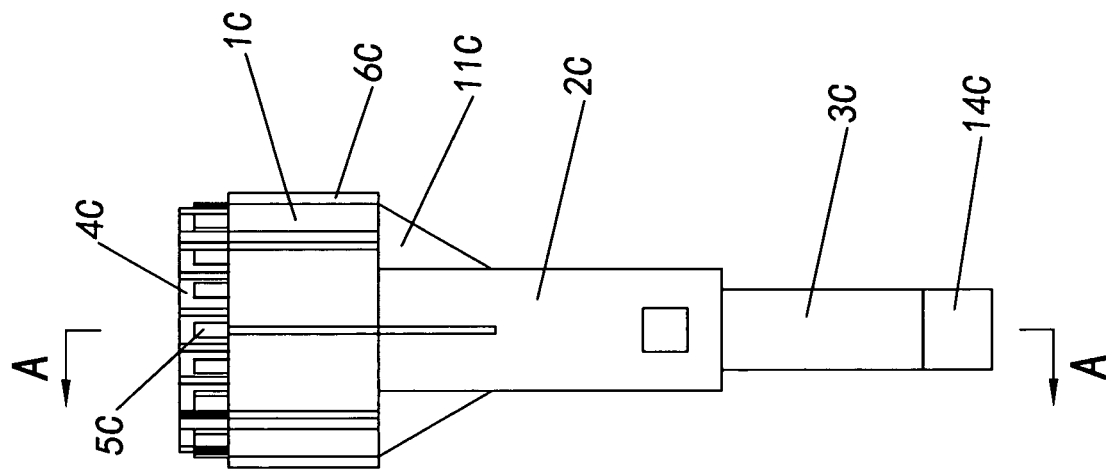
FIG. 14 illustrates a fourth preferred embodiment of the present invention.
Figure 16:
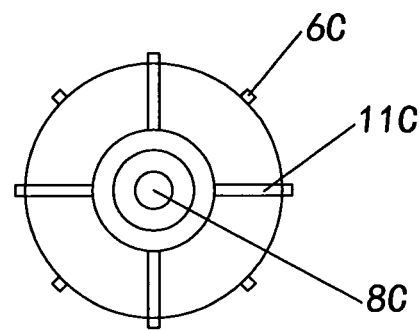
FIG. 16 is a bottom view of the fourth preferred embodiment of the present invention.
Figure 17:
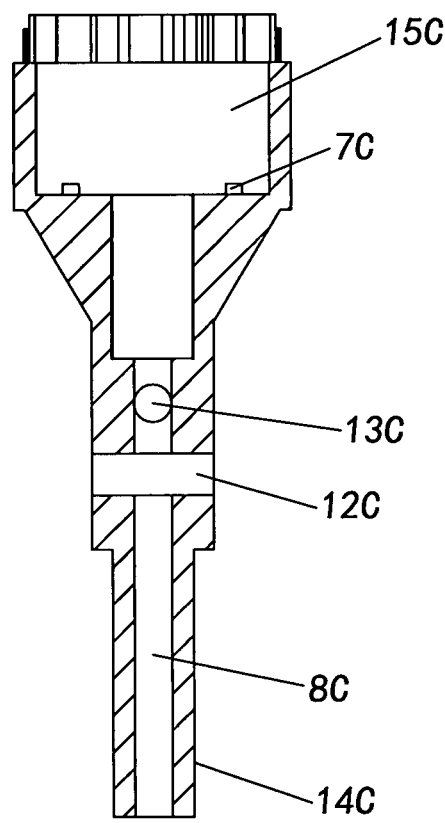
FIG. 17 is a sectional view of the fourth preferred embodiment of the present invention.

Referring to FIG. 12 to FIG. 13 of the drawings, a glans receiver socket according to a third embodiment of the present invention is illustrated, wherein the glans receiver socket has the advantages of one-piece structure and easy-operation.

The glans receiver socket comprise a glans socket 1B and a socket shaft 2B, wherein the glans socket 1B defines a glans chamber 110B for covering and protecting the glans of the patients. The glans socket 1B further comprises an annular flanging-rim 11B provided on the rim of the glans socket 1B, wherein the end face of the annular flanging-rim 11B is perpendicular to the axis of the glans socket 1B and forms a flanging surface. The socket shaft 2B is provided in the top portion of the outer surface of the glans socket 1B, and the axis of the socket shaft 2B and the axis of the glans socket 1B are located on the same axis.

The glans receiver socket further comprises at least one annular cutter slots 6B and at least one staples slots 5B, wherein the annular cutter slots 6B and the staples slots 5B are provided on the flanging surface 12B of the flanging-rim 11B. It is worth to mention that the arrangement of the staples slots 5B and the annular cutter slots 6B make the processing of bending staples easier.

More precisely, the annular cutter slots 6B are embodied as annular cutter slots surrounding the outer surface of the glans socket 1B, and when the number of the staples slots 5B chooses from 12 to 22, the staples slots 5B can perform a better effect. For example, in this embodiment, there are eighteen staple slots 5B evenly and spacedly formed on the flanging surface 12B and are provided at the rim of the inner side the flanging surface 12B.

If the number of the staples slots 5B is too few, it will reduce the effect of foreskin stitching. On the contrary, if the number of the staples slots 5B is too lager, it will difficult the machining process and higher the processing cost, also, too much staples will reduce the scalability of the foreskin. The number of the staples slots 5B depends on the size of the staples, in other words, the lager the staples means the less staple slots 5B, the smaller the staples means the more staples slots 5B.

Furthermore, the staples slots 5B further has two arc-shaped guiding surfaces 7B and a staple-press surface 8B, wherein the arc-shaped guiding surface 7B symmetrically provided on the two sides of the staple-press surface 8B.

It is worth to mention that the arrangement of the staples slots 5B and the arc-shaped guiding surface 7B can make the processing of the bending staples easy.

Also, the guiding rob 2B is embodied as a cylinder, the guiding rob 2B has an inner thread structure, that is to say, a set of threaded holes 3B are provided on the inner surface of the guiding rob 2B. Also, at least two positioning ribs 4B are provided on the cylindrical surface of the guiding rob 2B, wherein the positioning lib 4B can limit the rotation of the glans receiver socket.

Particularly, in this embodiment, there are eighteen positioning rids evenly and spacedly arranged on the cylindrical surface of the guiding rob 2B to limit the rotation of the glans receiver socket. The even and spacedly arranged manner of the positioning ribs 4B can not only reduce matching variation of the elements, but also increase the restricting effect of the positioning ribs, while enhancing the strength of the guiding shaft.

Furthermore, the glans receiver socket is embodied as a one-piece structure, in such way to save the manufacturing and the assembly cost of the glans receiver socket and also to solve the problem that the curved nail-foot ring is easy to fall off.

Referring to FIG. 14 to FIG. 17 of the drawings, a staple actuator according to a fourth preferred embodiment of the present invention is illustrated, wherein the staple actuator has a one-piece structure and can perform an auto spring-back effect.

The staple actuator is embodied as a ladder shaft, wherein a though hole 8C is set in the axis of the ladder shaft. In other words, the ladder shaft is a hollow structure and defines the though hole 8C in the axis of the ladder shaft. And the ladder shaft comprises a cutter-storage shaft 1C, a driving shaft 2C and a spring-back shaft 3C, and the cutter-storage shaft 1C, the driving shaft 2C and the spring-back shaft 3C are linked in order wherein the diameter of the cutter-storage shaft 1C, the driving shaft 2C and the spring-back shaft 3C is decreasing in sequence.

The cutter storage shaft 1C comprises at least one staple pusher arms 4C, a cutter storage 15C and at least one annual cutter fixed columns 7C.

The cutter storage shaft 1C comprises at least two staple pusher arms 4C, and the staple pusher arms 4C are evenly spaced on the end space of the cutter storage shaft 1C wherein the end space is far away from the driving shaft 2C. And when the number of the staple pusher arms 4C chooses from 12 to 22 the staple pusher arms 4C can perform a better effect. Preferably, the number of the staple pusher arms 4C is set as 18, and at least one staple pusher arm strengthens 5C are provided in the staple pusher arms 4C, the set of the staple pusher arm strengthens 5C can increase the intensity of the staple pusher arms 4C.

If the number of the staple pusher arms 4C is too few, it will reduce the effect of foreskin stitching. On the contrary, if the number of the staple pusher arms 4C is too large, it will difficult the machining process and higher the processing cost. Also, too much staples will reduce the scalability of the foreskin. The number of the staple pusher arms 4C depends on the size of the staples. In other words, the lager the staples is and the fewer staple pusher arms 4C are.

The cutter storage 15C is a cylindrical cavity provided on the inner of the cutter storage shaft 1C, and the annual cutter fixed columns 7C are provided on the bottom of the cutter storage shaft 1C, and the cutter storage shaft 1C comprises at least two annual cutter fixed columns 7C evenly spaced on the bottom of the cutter storage 15C. Preferably, in this embodiment, the number of the annual cutter fixed columns 7C is set as 4C.

Furthermore, at least two cutter storage shafts guiding reinforcements 6C are provided on the peripheral surface of the cutter storage shaft 1C. In other words, the cutter storage shaft 1C comprises at least two cutter storage shafts guiding reinforcements 6C, and the cutter storage shafts guiding reinforcements 6C are evenly spaced on the peripheral surface of the cutter storage shaft 1C.

The driving shaft 2C comprises a guiding hole 9C, at least one driving shaft guiding reinforcements 11C, a driving hole 12C and a limit hole 13C.

The guiding hole 9C is provided at the inner side of the driving shaft 2C and has same centre with the though hole 8C. In other words, the guiding hole 9C and the though hole 8C is concentric, and at least one guiding slots 10C is set in the circular surface of the guiding hole 9C. Particularly, the number of the guiding slots 10C is set as 10, and the guiding slots 9C are evenly spaced on the circular surface of the guiding holes.

The guiding hole 9C and the guiding slots 10C of the driving shaft 2C work with the glans receiver socket 10C, so as to limit the position of the glans receiver socket 10C.

The driving shaft guiding reinforcements 11C is set on the cylindrical surface of the driving shaft 2C and is connected with the cutter storage 1C. Particularly, the number of the driving shaft guiding reinforcements 11C is set as 4, and the driving shaft guiding reinforcements 11C are evenly spaced on the cylindrical surface of the driving shaft 2C.

The driving hole 12C is a though hole which is extended through the driving shaft 2C, wherein the driving hole 12C is provided at one side connected with the spring-back shaft 3C of the driving shaft 2C. Furthermore, the limit hole 13C is set on the cylindrical surface of the driving shaft 2C.

Also the driving hole 12C can match with the driving shaft of the operation handles 50C to make the usage become more easily and to larger the force arm.

And the end side of the spring-back shaft 3C set with outer thread 14C, in such a way that when a spring is fixed on the spring-back shaft 3C by an nut-connect, the other side of the spring is set with the outer shaft of the male circumcision, and once the operation handles is loosed, the staple actuator can perform an auto spring-back effect, the stitched foreskin can be back to the glans receiver socket automatically.

Figure 18:
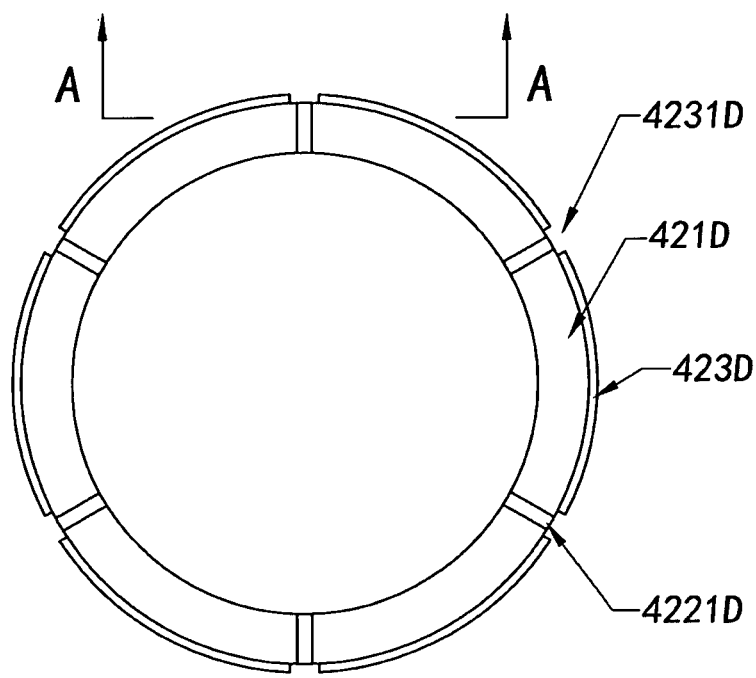
FIG. 18 illustrates a fifth preferred embodiment of the present invention.
Figure 19:
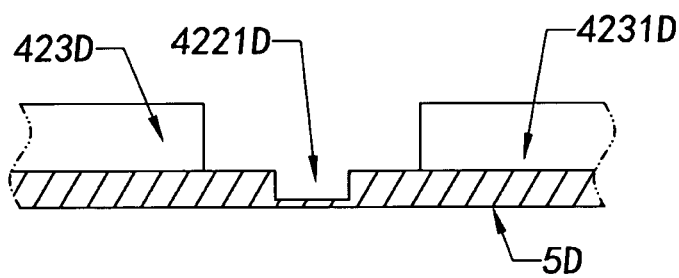
FIG. 19 is a sectional view of the holding band according to the fourth preferred embodiment of the present invention.
Figure 20:
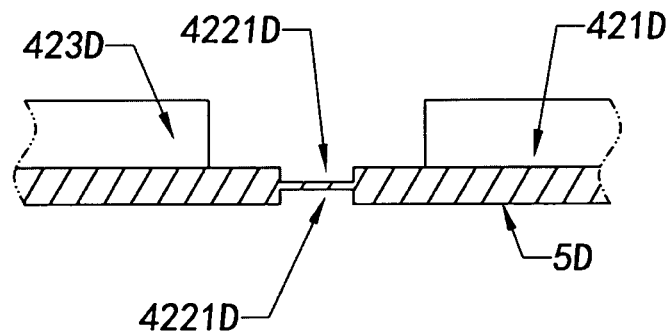
FIG. 20 is another sectional view of the holding band according to the fourth preferred embodiment of the present invention.

Referring to FIG. 18 to FIG. 20 of the drawings, a device for male circumcision and suture according to a fifth embodiment, which is an alternative mode of the first embodiment, is illustrated, wherein the structural configuration of the third embodiment is the substantially the same as that of the first embodiment, expect the suture cartridge 40D. Accordingly, the suture cartridge 40D comprises a plurality of staples 41D disposed at the front edge 201D of the operation housing 20D, wherein when the staples 41D are pushed out of the front edge 201D of the operation housing 20D, the staples 41D are pushed to penetrate through the excess foreskin of the patient at the cut area thereof for applying the stitches to the cut area of the skin. Each of the staples 41D, having a U-shaped configuration, has a staple body 411D and two staple pins 412D, wherein when the staple is pushed to the guiding seat, the staple pins 412D are guided and bent by the staple guiding indentation of the outer seat portion of the guiding seat for stitching the cut area of the skin.

Accordingly, the suture cartridge 40D further comprises an annular holding band 42D that the staples 41D are evenly disposed therearound, such that when the staples 41D are pushed for penetrating the staple pins through the skin to stitch the cut area of the skin, the holding band 42D is correspondingly pushed to encircle around the cut area of the skin, thereby applying pressure at the cut area of the foreskin for preventing bleeding. It is worth mentioning that when the staples 41D are pushed for penetrating the staple pins through the skin to stitch the cut area of the skin, the holding band 42D is correspondingly pushed to encircle around the cut area of the skin. Therefore, the holding band 42D also serves as a cushioning element to absorb any excessive penetrating force of each of the staples 41D during the stitching operation. In other words, the holding band 42D not only ensures the corrected alignment of the staples 41D to be evenly spaced apart with each other but also provides a buffering clearance between the staples 41D and the cut area of the patient so as to prevent the direct stapling contact of the staples 41D to the cut of the patient.

Conventionally, the holding band 42D encircling around the cut area of the foreskin is made of poorly retractable material, that is to say, the conventional holding band 42D has a substantially fixed size, making it troublesome to emit urination for the patient. Even worse, the cut area on the foreskin might be tore to bleed for the reason that the physiologically erected penis is sufferingly restricted by the conventional fixed-sized holding band 42D. The holding band 42D provided in this preferred embodiment has a good retractable ability, which is able to substantially overcome the aforementioned shortcomings so as to improve the patient experience.

Referring to FIG. 18 of the drawings, the holding band 42D further comprises an annular holding body 421D and at least a retraction means 422D provided at the annular holding body 421D. The holding band 42D in this preferred embodiment is made of medical silicone rubber, that's to say, the annular holding body 421D has a good resilient ability, wherein the retraction means 422D provided at the annular holding body 421D is able to further enhance the resilient ability of the holding band 42D, such that the holding band 42D is capable of incorporating with various size of pines retractably and fittingly.

More specifically, there are at least two retraction means 422D evenly formed at the annular holding body 421D, wherein the retraction means 422D is embodied as retraction slot 4221D in some embodiments of the present invention. In other words, there are at least two retraction slot 4221D indently formed on the annular body, wherein the thickness of the annular body at the retraction slot 4221D is substantially minimized to enhance the retractable ability of the holding band 42D thereby.

In some embodiment of present invention, the retraction slot 4221D evenly distributed around the annular body has a cross section of convex polygon shape, such as triangle, quadrilateral, pentagon, and etc, wherein the convex polygon shaped retraction slot 4221D is longitudinally and indently extended from the inner side towards the outer side of the annular body. It is important to mention that the shape of the cross section is not a limit of the represent invention, wherein the retraction slot 4221D might has a curved shape, such as semi-circular, semi-elliptical, and etc.

In some embodiments of the present invention, the retraction slots 4221D can be formed merely on the top surface of the annular holding body 421D or merely on the bottom surface of the annular holding body 421D, wherein the retraction slots 4221D are symmetrically distributed with respective to the center of the annular holding body 421D, in such a manner that the load applied on the holding band 42D is evenly adsorbed via the retraction slots 4221D respectively. It is important to mention that the retraction slots 4221D can be both arranged on the bottom surface and top surface for further enhancing the retractable ability of the holding band 42D, wherein the retraction slots 4221D distributed on top surface is arranged symmetrically to the retraction slots 4221D provided on the bottom surface.

Preferably, the amount of the retraction slots 4221D is ranged from 4 to 8. As such that the retractions slots are capable of enhancing the retractable ability to a suitable level, while the manufacturing cost and complexity are within an acceptable level.

As mentioned in the first preferred embodiment, the holding band 42D is received within a retention seat 22D of the operation housing 20D, wherein the retention seat 22D is indently formed around the front edge 201D thereof. In order to conveniently and securely mount the holding band 42D at the retention seat 22D, the handing band further has a positioning edge 423D extended from the outer side of the annular holding body 421D, which is arranged to engaged within the retention seat 22D for precisely aligning and affixing the annular holding body 421D at the predetermined position thereof. It is important to mention that since the holding band 42D is securely embedded into the retention seat 22D, that the worry of unintentionally detachment of the holding band 42D from the retention seat 22D is substantially eliminated.

There is a plurality of notches 4231D formed on the positioning edge 423D of the holding body 421D for breaking the positioning edge 423D thereat, such that the retraction slot 4221D formed on the annular is able to function well in enhancing the retractable ability of the holding band 42D. In other words, the integration of the positioning edge 423D is broken by the notches 4231D formed there at, enabling external force applied on the holding band 42D to propagate along the retraction slot 4221D to expand the holding band 42D.

Preferably, the notches 4231D provided on the positioning edge 423D are located corresponding to the arrangement of the retraction slots 4221D, that is to say, the amount of the notches 4231D matches with the retraction slots 4221D. More preferably, each of the notches 4231D has a substantially same cross section shape with the retraction slot 4221D, while the width of the notch is larger than that of the retraction slot 4221D, such that the notches 4231D are able to provide a free outlet allowing the holding band 42D to expand via the retraction slots 4221D thereof.

Referring to FIG. 19, a specific embodiment of the holding band 42D is illustrated, wherein the holding band 42D further comprises an annular holding body 421D and six retraction slots 4221D evenly formed on the top surface of the annular holding body 421D, wherein the retraction slot 4221D has a rectangle cross section shape.

Moreover, the holding band 42D further comprises a positioning edge 423D extended from the outer side of the annular holding body 421D, with six notches 4231 formed on the positioning edge 423D of the holding body 421D for breaking the positioning edge 423D thereat. The notches 4231D provided on the positioning edge 423D are located corresponding to the arrangement of the retraction slots 4221D, wherein each of the notches 4231D has a substantially same cross section shape with the retraction slot 4221D, with a width larger than that of the retraction slot 4221D.

Referring to FIG. 20, another specific embodiment of the holding band 42D is illustrated, wherein the holding band 42D further comprises an annular holding body 421D and six retraction slots 4221D evenly formed on the top and bottom surfaces of the annular holding body 421D respectively, wherein each of the retraction slots 4221D has a rectangle cross section shape. It is important to mention that the retraction slots 4221D distributed on top surface are arranged symmetrically to the retraction slots 4221D provided on the bottom surface.

Moreover, the holding band 42D further comprises a positioning edge 423D extended from the outer side of the annular holding body 421D, with six notches 4231 formed on the positioning edge 423D of the holding body 421D for breaking the positioning edge 423D thereat. The notches 4231 provided on the positioning edge 423D are located corresponding to the arrangement of the retraction slots 4221D, wherein each of the notches 4231D has a substantially same cross section shape with the retraction slot 4221D, with a width larger than that of the retraction slot 4221D.

Figure 21:
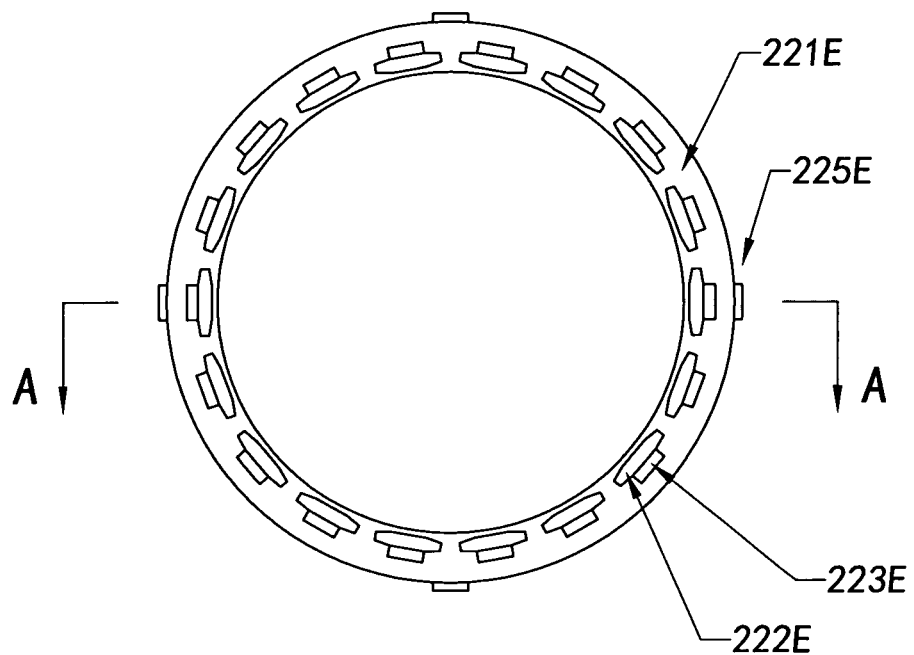
FIG. 21 is a top view of a sixth preferred embodiment of the present invention.
Figure 22:
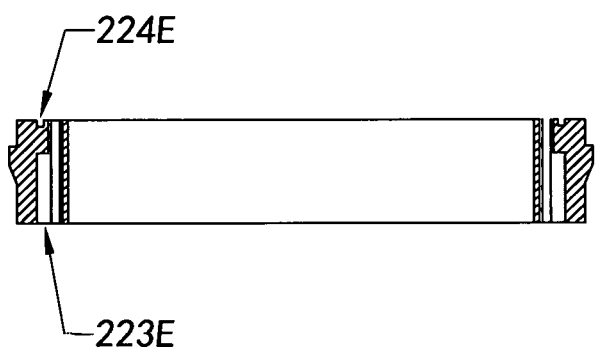
FIG. 22 is a sectional view of the sixth preferred embodiment of the present invention.

Referring to FIG. 21 to FIG. 22, a device for male circumcision and suture according to a sixth embodiment, which is an alternative mode of the first embodiment, is illustrated, wherein the structural configuration of the third embodiment is the substantially the same as that of the first embodiment, expect the retention seat 22E arranged for receiving a holding band 42E and staples 41E in the present invention.

Accordingly, the retention seat 22E is provided around the front edge 201E of the operation housing 20E to receive the holding band 42E and staples 41E therewithin, wherein when the staples 41E are actuated by the staple pusher arms 633E of the staple actuator 63E, the staples 41E are pushed for penetrating the staple pins 412E through the foreskin to stitch the cut area thereof, while the holding band 42E is correspondingly pushed to encircle around the cut area thereof, as mentioned in the first preferred embodiment.

The retention seat 22E further comprises an annular member body 221E having a front end surface 2210E and a rear end surface 2211E, wherein a plurality of staple guiding slots 222E are formed on front end for receiving the staples 41E respectively and a plurality of reinforcing slots 223E extended from the side surface of the staple guiding slots 222E respectively.

It is important to mention that the staple guiding slots 222E are through holes extended from the front end surface 2210E to the rear end surface 2211E to incorporate with staples 41E arm in such a manner that when the staples 41E arm is actuated by the operation handles, the staples 41E arms are moved to extend into the staple guiding slots 222E and the reinforcing slots 223E respectively to contact with staples 41E, so that the staples 41E are pushed out of the front edge 201E of the operation housing 20E to the guiding seat 112E of the glans socket 11 for applying the stitches at the cutter area of the patient.

Conventionally, the staple guiding slot 222E is a narrow and elongated slot formed through the annular member body 221E, such that the staple arm of the staple actuator 63E has to be designed in a corresponding elongated and narrow configuration, such as bar, to slidably engage into the staple guiding slot 222E for moving the staples 41E. As such, the staples 41E arm has a relative thin structure with poor strength, so that contact surface and pushing effect between the staples 41E and the staple pusher arms 633E are not sufficient enough in some embodiment, causing the staples 41E stuck and inconvenient operations.

Accordingly, in this preferred embodiment, the staple guiding slot 222E has a substantially oval cross section having two larger end portion and a relative smaller portion extended therebetween so as to enlarge the space of the staple guiding slot. Moreover, the reinforcing slots 223E integrally formed at the side surface of the staple guiding slot 222E further maximize the space of the staple guiding slot 222E, such that the staples 41E arm can be thickened to have a relative thin structure with strengthened strength. As such that contact surfaces and pushing effect between the staples 41E and the staple pusher arms 633E are enhanced for preventing the staples 41E stuck into the staple pusher arms 633E so as to secure and simplify the operation thereof.

It is important to mention that the amount of the staple guiding slot is ranged from 12 to 22. As such that the staples 41E disposed within the staple guiding slots 222E are capable of providing a satisfactory stitches at the cutter area of the patient while keeping the cost and manufacturing of the staples 41E within an economic level. It is important to mention that the amount of the staples 41E is associated with the size thereof: the larger the staples 41E are, the fewer the staples 41E would be.

Furthermore, the annular member body 221E of the retention seat 22E further forms a rband receiving slot 224E on the rear end surface 2211E of the annular member body 221E, wherein the banding receiving slot 224E is arranged at a position between the outer surface of the annular member body 221E and the staple guiding slot 222E. During use, the holding band 42E is aligned with and mounted into the band receiving slot 224E in an embedded manner, so that the alignment and positioning of the holding band 42E to the retention seat 22E is substantially simplified while the worry of unintentional to detachment of the holding band 42E is substantially eliminated.

Furthermore, at least two positioning protrusions 225E are evenly formed on the outer surface of the annular member body 221E, so that when the retention seat 22E is detachably mounted at the front edge 201E of the operation housing 20E, the positioning protrusions 225E guide the alignment between the retention seat 22E and the operation housing 20E for preventing the misalignment between the staple pusher arms 633E and staple guiding slot 222E.

Referring to FIG. 21 to FIG. 22, a specific embodiment of the retention seat 22E is illustrated, wherein the retention seat 22E further comprises annular member body 221E having a front end surface 2210E and a rear end surface 2211E, wherein eighteen staple guiding slots 222E are evenly formed on front end surface 2210E for receiving the staples 41E respectively and eighteen reinforcing slots extended from the side surface of the staple guiding slots 222E respectively.

The staple guiding slot 222E has a substantially oval cross section having two larger end portion and a relative smaller portion extended therebetween so as to enlarge the space of the staple guiding slot.

Furthermore, the annular member body 221E of the retention seat 22E further forms a rband receiving slot 224E on the rear end surface 2211E of the annular member body 221E, wherein the rband receiving slot 224E is arranged at a position between the outer surface of the annular member body 221E and the staple guiding slot 222E.

There are four positioning protrusions 225E are evenly formed on the outer surface of the annular member body 221E, so that when the retention seat 22E is detachably mounted at the front edge 201E of the operation housing 20E, the positioning protrusions 225E guides the alignment between the retention seat 22E and the operation housing 20E for preventing the misalignment between the staple pusher arms 633E and staple guiding slot 222E.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A device for male circumcision and suture, comprising:
   a glans receiver socket which comprises a glans socket for inserting into and placed underneath an excess foreskin of a patient to cover a glans thereof, and a socket shaft extended from said glans socket, wherein said glans socket has a guiding seat coaxially aligned with said socket shaft;
   a hollow operation housing having a circular front edge, a rear edge, and a shaft channel extended from said front edge to said rear edge, wherein said socket shaft slidably passes through said shaft channel until said front edge of said operation housing is biased against said guiding seat of said glans socket for retaining the excess foreskin of the patient between said front edge of said operation housing and said guiding seat of said glans socket;
   an annular cutter coaxially coupled at said front edge of said operation housing;
   a suture cartridge which comprises a plurality of staples spacedly disposed at said front edge of said operation housing, and an annular holding band that said staples are evenly disposed therearound, wherein each of said staples, having a U-shaped configuration, has a staple body and two staple pins being bent for stitching a cut area of the patient, wherein sharp ends of said staple pins of each of said staples are slightly penetrated into said holding band to retain said holding band at said front edge of said operation housing and line up said plurality of staples, such that said staples are held by said holding band in a circular configuration at said front edge of said operation housing;
   two operation handles pivotally coupled at said operation housing to actuate said annular cutter and said suture cartridge at the same time by applying pressing forces at said operation handles respectively after said glans receiver socket is locked for retaining the excess foreskin of the patient between said front edge of said operation housing and said guiding seat of said glans socket, wherein when said operation handles are concurrently and pivotally moved towards said operation housing, a cutting edge of said annular cutter is pushed out of said front edge of said operation housing to contact with said guiding seat of said glans socket for removing the excess foreskin of the patient and at the same time, said staples are pushed away from said front edge of said operation housing towards said guiding seat at a position that said sharp ends of said staple pins of each of said staples are penetrated through said holding band to contact with said guiding seat of said glans socket for applying stitches at the cut area of the excess foreskin of the patient, wherein said holding band is pushed out of said front edge of said operation housing by said staples for encircling around the cut area at the same time when said staples are arranged for stitching at the cut area of the patient, such that said holding band not only ensures a corrected alignment of said staples to be evenly spaced apart with each other but also provides a buffering clearance between said staples and the cut area of the patient so as to prevent a direct stapling contact of said staples to the cut area of the patient, wherein each of said operation handles is made of breakable material having a safety factor for preventing an over-pressing force applied thereon, such that said operation handle is broken when said pressing force is lamer than said safety factor; and
   a locking mechanism provided at said operation housing for releasably locking pivotal movements of said operation handles.

2. The device, as recited in claim 1, wherein said operation housing further comprises a locking body provided thereat to form said rear edge at said locking body and releasably locked up with said socket shaft for ensuring the excess foreskin of the patient to be securely retained between said front edge of said operation housing and said guiding seat of said glans socket before said operation handles are pivotally moved to actuate said annular cutter and said suture cartridge.

3. The device, as recited in claim 2, wherein said locking body has an inner threaded structure rotatably engaging with an outer threaded structure provided at a free end portion of said socket shaft, such that when said socket shaft is slid into said shaft channel, said locking body is rotated to engage said inner threaded structure with said outer threaded structure of said socket shaft so as to lock up said glans socket at said front edge of said operation housing.

4. The device, as recited in claim 1, wherein said socket shaft is extended through said shaft channel of said operation housing until a free end of said socket shaft is aligned with a rear end face of said shaft channel to ensure a placement of said glans receiver socket.

5. The device, as recited in claim 1, further comprising an alignment means for aligning said socket shaft to be slid into said shaft channel, wherein said alignment means comprises an alignment rib radially protruded from said socket shaft and an alignment slot indented on a surrounding wall of said shaft channel, such that when said socket shaft is slid into said shaft channel, said alignment rib is alignedly engaged with said alignment slot to ensure a corrected alignment of said glans receiver socket.

6. The device, as recited in claim 1, wherein each of said operation handles has a pivot end pivotally coupled at said operation housing and a free end extended toward said rear edge of said operation housing, such that said free ends of said operation handles are moved toward said operation housing to actuate said annular cutter and said suture cartridge at the same time.

7. The device, as recited in claim 1, wherein when said holding band is disposed at said front edge of said operation housing, said staples are automatically lined up therearound, wherein said holding band is made of resilient material, such that said sharp ends of each of said staples are pushed to penetrate through said holding band.

8. The device, as recited in claim 7, wherein said operation housing further has a retention seat indently formed around said front edge thereof to receive said holding band within said retention seat.

9. The device, as recited in claim 1, further comprising a plurality of staple pusher arms movably coupled at said front edge of said operation housing, wherein said staple pusher arms are actuated by said operation handles to push said staples to said guiding seat of said glans socket and at the same time to push said holding band for encircling the cut area.

10. The device, as recited in claim 1, wherein said staples are disposed around said front edge of said operation housing to coaxially align with said annular cutter at a position that said annular cutter is located within said staples.

11. The device, as recited in claim 1, wherein said glans socket has a conical shape for covering the glans of the patient, wherein said socket shaft is extended from an apex of said glans socket.

12. The device, as recited in claim 1, further comprising an actuation unit for driving said annular cutter and said suture cartridge at the same time, wherein said actuation unit comprises a driving shaft movably disposed in said operation housing, a driving arm unit operatively linked between said operation handles and said driving shaft to drive said driving shaft to slide within said operation housing, and a staple actuator coupled with said driving shaft for pushing said annular cutter and said suture cartridge at the same time.

13. The device, as recited in claim 12, wherein said actuation unit further comprises a resilient element biased against said driving shaft to push said staple actuator away from said annular cutter and said suture cartridge, wherein said resilient element, which is a compression spring, applies a resilient force against said driving shaft to prevent a pivotal actuation of each of said operation handles.

14. The device, as recited in claim 13, wherein said driving shaft further comprises a shaft stopper coupled at an end portion of said driving shaft, wherein said resilient element is coaxially coupled at said driving shaft at a position that two ends of said resilient element are biased against said shaft stopper and a stopper shoulder which is inwardly protruded from an inner circumferential wall of said shaft channel.

15. The device, as recited in claim 14, wherein said resilient element is pre-compressed to be retained along a tail body of said driving shaft between said shaft stopper and said stopper shoulder, and is further compressed when said operation handles are pivotally moved at said operation housing to actuate said annular cutter and said suture cartridge at the same time.

16. The device, as recited in claim 15, wherein said driving arm unit comprises two actuating arms integrally extended from two inner ends of said operation handles to pivotally couple at said driving shaft, wherein said driving arm unit further has two actuating slots indentedly formed at the driving shaft, wherein two inner ends of said actuating arm are extended into said shaft channel to engage with said actuating slots respectively.

\* \* \* \* \*